(12) United States Patent
Walt et al.

(10) Patent No.: US 6,482,593 B2
(45) Date of Patent: *Nov. 19, 2002

(54) FIBER OPTIC BIOSENSOR FOR SELECTIVELY DETECTING OLIGONUCLEOTIDE SPECIES IN A MIXED FLUID SAMPLE

(75) Inventors: David R. Walt, Lexington, MA (US); Brian G. Healey, Guilford, CT (US)

(73) Assignee: Trustees of Tufts College, Medford, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/187,289

(22) Filed: Nov. 5, 1998

(65) Prior Publication Data

US 2002/0009719 A1 Jan. 24, 2002

Related U.S. Application Data

(63) Continuation of application No. 08/851,203, filed on May 5, 1997.

(51) Int. Cl.[7] ............................ C12Q 1/68; C12P 19/34; C07H 21/02

(52) U.S. Cl. .................. 435/6; 435/91.2; 536/23.1; 536/24.3; 422/55; 422/68.1; 422/82.05; 422/82.06; 422/82.07; 422/82.08; 65/409

(58) Field of Search .................. 435/6, 91.2; 536/23.1, 536/24.3; 422/55, 68.1, 82.05, 82.06, 82.07, 82.08; 65/409

(56) References Cited

U.S. PATENT DOCUMENTS

| | | |
|---|---|---|
| 4,200,110 A | 4/1980 | Peterson et al. |
| 4,499,052 A | 2/1985 | Fulwyer |
| 4,682,895 A | 7/1987 | Costello |

(List continued on next page.)

FOREIGN PATENT DOCUMENTS

| | | |
|---|---|---|
| EP | 0269764 A1 | 6/1988 |
| EP | 0 392 546 | 10/1990 |
| EP | 0478319 A1 | 4/1992 |
| EP | 0723146 A1 | 7/1996 |
| WO | WO8911101 A | 11/1989 |
| WO | WO9302360 A | 2/1993 |
| WO | 96/03212 | 2/1996 |

(List continued on next page.)

OTHER PUBLICATIONS

Czarnik, "Illuminating the SNP Genomic Code," Modern Drug Discovery, 1(2): 49–55 (1998).

Drmanac, R. et al., "Sequencing by Oligonucleotide Hybridization: A Promising Framework in Decoding of the Genome Program," The First International Conference on Electrophoresis, Supercomputing and the Human Genome, Proceeding os th Apr. 10–13, 1990 Conference at Florida State University. Ed. C. Cantor and H. Lim.

(List continued on next page.)

Primary Examiner—Jeffrey Fredman
(74) Attorney, Agent, or Firm—Flehr Hohbach Test Albritton & Herbert LLP; Robin M. Silva; David C. Foster

(57) ABSTRACT

The present invention provides biosensors, apparatus and methods for selectively detecting at least one complementary oligonucleotide target specie in a fluid sample containing a mixture of different oligonucleotide fragments. One preferred embodiment of the biosensor is as a unitary fiber optic array having species of single stranded nucleic acid disposed as individual deposits in aligned organization upon multiple strand end faces at differing spatial positions on the distal array end surface.

19 Claims, 18 Drawing Sheets

U.S. PATENT DOCUMENTS

| | | |
|---|---|---|
| 4,785,814 A | 11/1988 | Kane |
| 4,822,746 A | 4/1989 | Walt |
| 4,824,789 A | 4/1989 | Yafuso et al. |
| 4,999,306 A | 3/1991 | Yafuso et al. |
| 5,002,867 A | 3/1991 | Macevicz |
| 5,028,545 A | 7/1991 | Soini |
| 5,105,305 A | 4/1992 | Betzig et al. |
| 5,114,864 A | 5/1992 | Walt |
| 5,132,242 A | 7/1992 | Cheung |
| 5,143,853 A | 9/1992 | Walt et al. |
| 5,194,300 A | 3/1993 | Cheung |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,302,509 A | 4/1994 | Cheeseman |
| 5,320,814 A | 6/1994 | Walt et al. |
| 5,357,590 A | 10/1994 | Auracher |
| 5,380,489 A | 1/1995 | Sutton et al. ............... 422/68.1 |
| 5,435,724 A | 7/1995 | Goodman et al. |
| 5,481,629 A | 1/1996 | Tabuchi |
| 5,494,798 A | 2/1996 | Gerdt et al. |
| 5,496,997 A | 3/1996 | Pope |
| 5,512,490 A | 4/1996 | Walt et al. |
| 5,516,635 A | 5/1996 | Ekins et al. |
| 5,565,324 A | 10/1996 | Still et al. |
| 5,571,639 A * | 11/1996 | Hubbell et al. ................ 430/5 |
| 5,573,909 A | 11/1996 | Singer et al. |
| 5,575,849 A | 11/1996 | Honda et al. |
| 5,633,972 A | 5/1997 | Walt et al. |
| 5,639,603 A | 6/1997 | Dower et al. |
| 5,656,241 A | 8/1997 | Seifert et al. |
| 5,690,894 A | 11/1997 | Pinkel et al. |
| 5,814,524 A | 9/1998 | Walt et al. |
| 5,840,256 A | 11/1998 | Demers et al. |
| 5,854,684 A | 12/1998 | Stabile et al. |
| 5,863,708 A | 1/1999 | Zanzucchi et al. |
| 5,888,723 A | 3/1999 | Sutton et al. .................. 435/5 |
| 5,900,481 A | 5/1999 | Lough et al. .............. 536/55.3 |
| 6,023,540 A | 2/2000 | Walt et al. |

FOREIGN PATENT DOCUMENTS

| | | |
|---|---|---|
| WO | 97/14028 | 4/1997 |
| WO | WO9714928 A | 4/1997 |
| WO | 97/40385 | 10/1997 |
| WO | 98/40726 | 9/1998 |
| WO | 98/53093 | 11/1998 |
| WO | 98/53300 | 11/1998 |
| WO | 99/67414 | 12/1999 |
| WO | 00/04372 | 1/2000 |

OTHER PUBLICATIONS

Drmanac, R. et al., "Prospects for a Miniaturized, Simplified and Frugal Human Genome Project," Scientia Yugoslavica, 16(1–2):97–107 (1990).

Drmanac, R. et al., "Sequencing by Hybridization (SBH) with Oligonucleotide Probes as an Integral Approach for the Analysis of Complex Genomes," International Journal of Genome Research, 1(1):59–79 (1992).

Drmanac, R. et al., "Sequencing by Hybridization," Automated DNA Sequencing and Analysis, ed. M. Adams, C. Fields and J. Venter. (1994).

Walter, D. "Fiber Optic Imaging Sensors," Accounts of Chemical Research, 31(5): 267–278 (1998).

Barnard et al., "A Fibre–Optic Chemical Sensor with Discrete Sensing Sites," Nature, 353:338–340 (Sep. 1991).

Fuh et al., "Single Fibre Optic Fluorescence pH Probe," Analyst, 112:1159–1163 (1987).

Grazia et al., "In–Vivo Biomedical Monitoring by Fiber–Optic Systems," Journal of Lightwave Technology, 13(7):1396–1406 (1995).

Hirschfeld et al., "Laser–Fiber–Optic "Optrode" for Real Time In Vivo Blood Carbon Dioxide Level Monitoring," Journal of Lightwave Technology, LT–5(7):1027–1033 (1987).

Peterson et al., "Fiber–Optic Sensors for Biomedical Applications," Science, 13:123–127 (1984).

U.S. application No. 08/818,199, Walt, et al., filed Mar. 14, 1997.

U.S. application No. 08/851,203, Walt, et al., filed May 5, 1997.

U.S. application No. 08/944,850, Walt, et al., filed Oct. 6, 1997.

U.S. application No. 09/033,462, Walt, et al., filed Mar. 2, 1998.

U.S. application No. 09/151,877, Walt, et al., filed Sep. 11, 1998.

E.J.A.Pope, "Fiber Optic Chemical Microsensors Employing Optically Active Silica Microspheres", SPIE, v2388, p245–256 (1995).

J.I.Peterson, et al., "Fiber Optical pH Probe for Physiological Use", Anal. Chem., v52, No. 6, May 1980, p864–869.

Anonymous, "Fluorescent Microspheres", Tech Note 19, Bang Laboratories, (Fishers, IN) Feb. 1997.

L.B.Bangs, "Immunological Applications of Microspheres", The Latex Course, Bangs Laboratories (Carmel, IN) Apr. 1996.

Anonymous, "Microsphere Selection Guide", Bangs Laboratories (Fishers, IN) Sep. 1998.

J.A. Ferguson, et al., "A Fiber–Optic DNA Biosensor Microarray for the Analysis of Gene Expression", Nature Biotechnology, v. 14, pp. 1681–1684 (Dec. 1996).

B.G. Healey, et al., "Fiber Optic DNA Sensor Array Capable of Detecting Point Mutations", Analytical Biochemistry, v. 251, No. 2, pp. 270–279 (1997).

B.G. Healey, et al., "Development of a Penicillin Biosensor Using a Single Optical Imaging Fiber", SPIE Proc., v. 2388, pp. 568–573 (1995).

B.G. Healey, et al., Improved Fiber–Optic Chemical Sensor for Penicillin, Anal. Chem, v. 67, No. 24, pp. 4471–4476 (Dec. 15, 1995).

D.R. Walt, "Fiber–Optic Sensors for Continuous Clinical Monitoring", Proc. IEEE, v.80, No. 6, pp. 903–911 (Jun. 1992).

N.J.C. Strachan, et al., "A Rapid General Method for the Identification of PCR Products Using a Fibre–Optic Biosensor and Its Application to the Detection of Listeria", Ltrs. Applied Microbiology, v. 21, pp. 5–9 (1995).

P.A.E. Piunno, et al., "Fiber–Optic DNA Sensor for Fluorometric Nucleic Acid Determination", Anal. Chem., v. 67, pp. 2635–2643 (1995).

A.P. Abel, et al., "Fiber Optic Evanescent Wave Biosensor for the Detection of Oligonucleotides", Anal. Chem., v. 68, No. 17, pp. 2905–2912 (Sep. 1, 1996).

P. Pantano, et al., "Ordered Nanowell Arrays", Chem. Mater., v. 8, No. 12, pp. 2832–2835 (1996).

K.L. Michael, et al., "Fabrication of Micro– and Nanostructures Using Optical Imaging Fibers and there Use as Chemical Sensors", Proc. 3rd Intl. Symp., Microstructures and Microfabricated Systems, ed. P.J. Hesketh, et al., v. 97–5, Electrochem. Soc., pp. 152–157 (Aug. 1997).

K.L. Michael, et al., "Making Sensors out of Disarray: Optical Sensor Microarrays", Proc. SPIE, v. 3270, pp. 34–41 (1998).

K.L. Michael, et al., "Randomly Ordered Addressable High–Density Optical Sensor Arrays", Anal. Chem., v. 70, No. 7, pp. 1242–1248 (Apr. 1998).

* cited by examiner

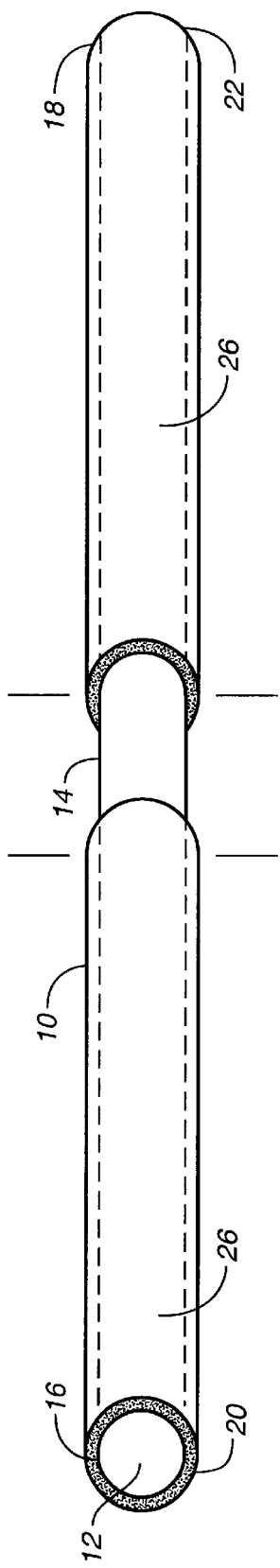
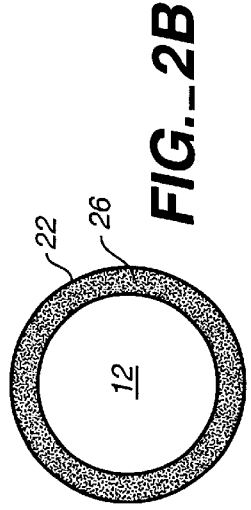
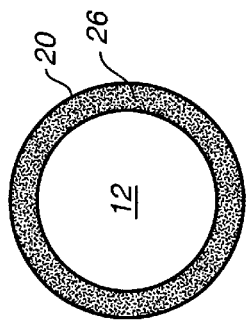
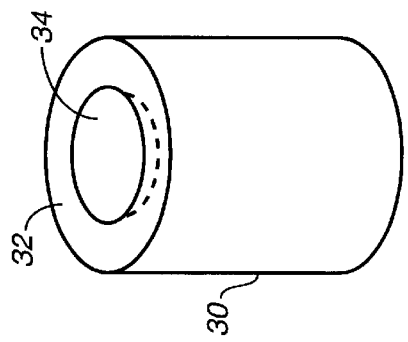
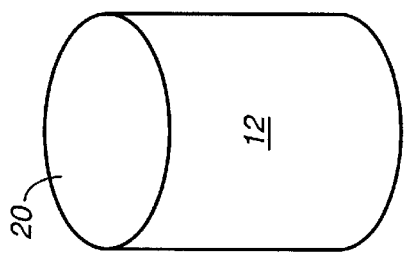

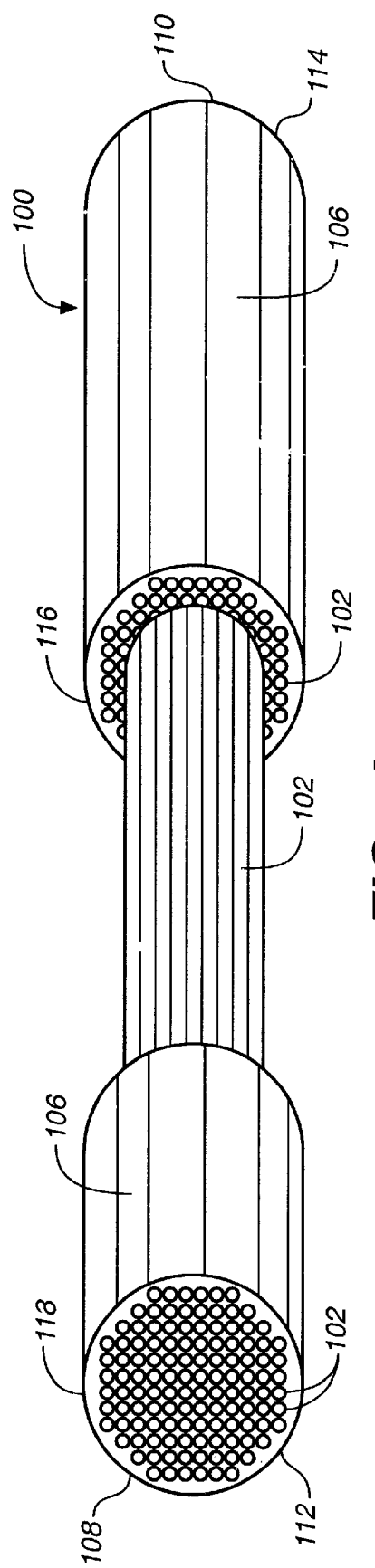
FIG._4

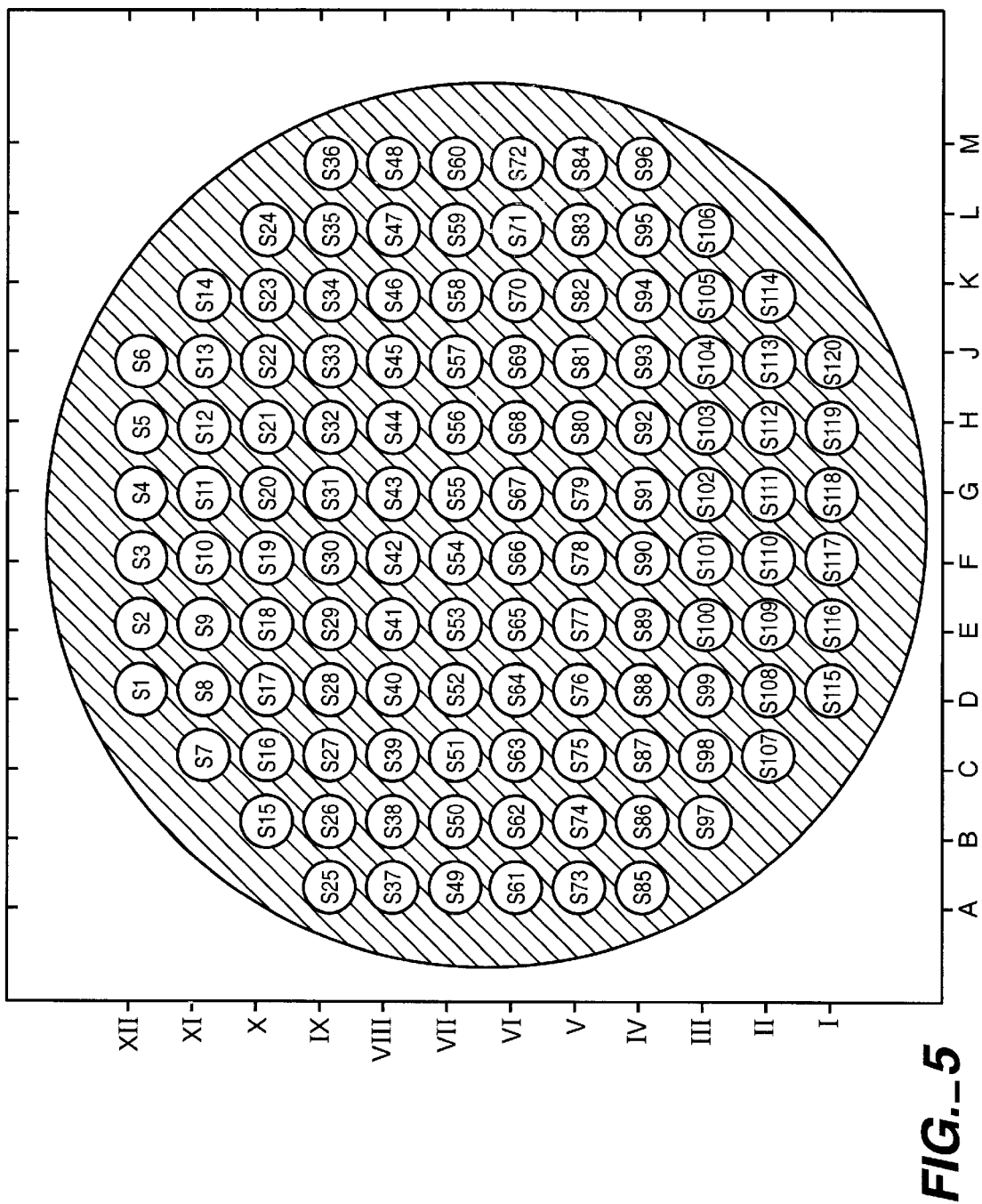
FIG._5

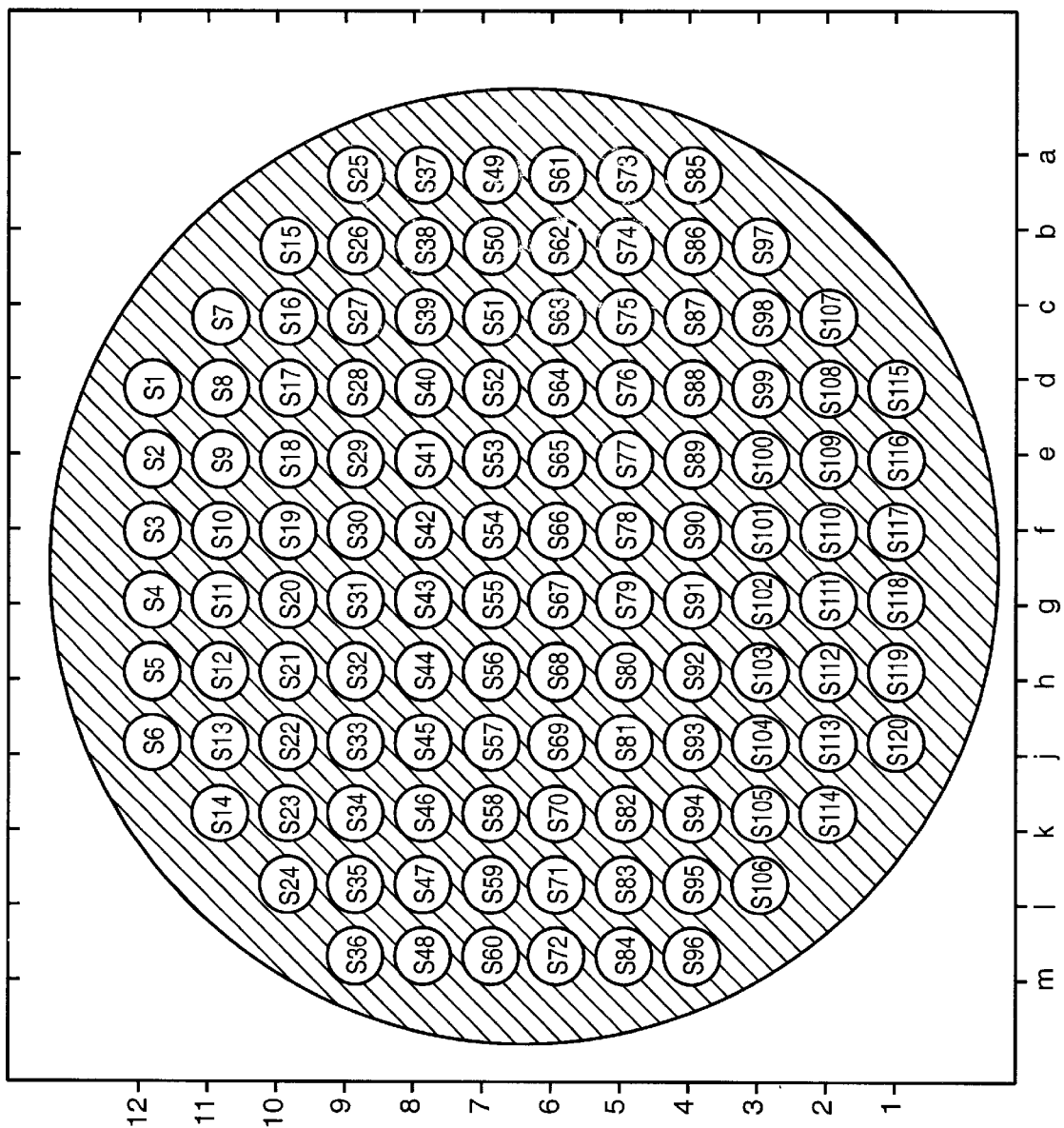
FIG._6

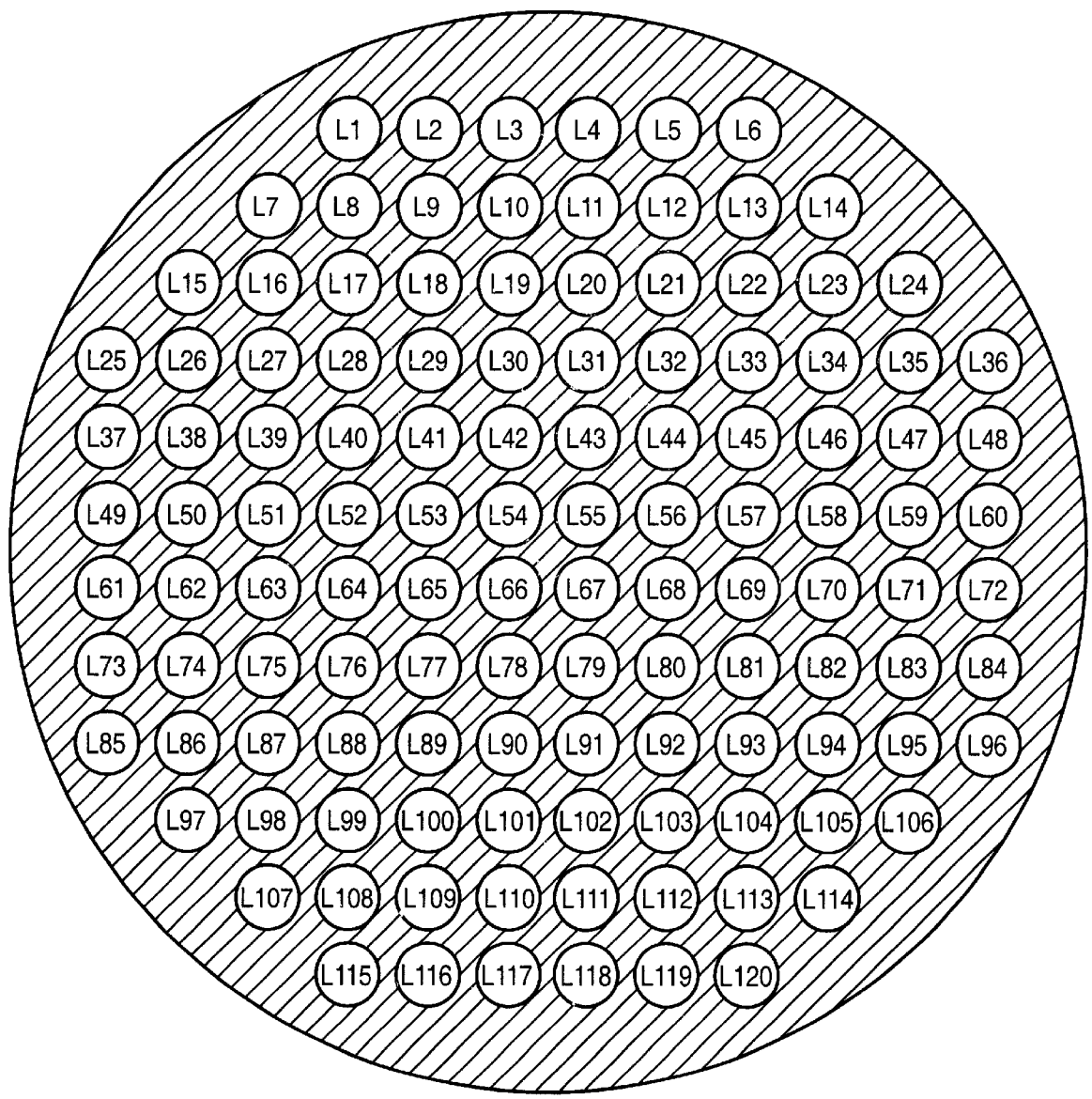
FIG._7

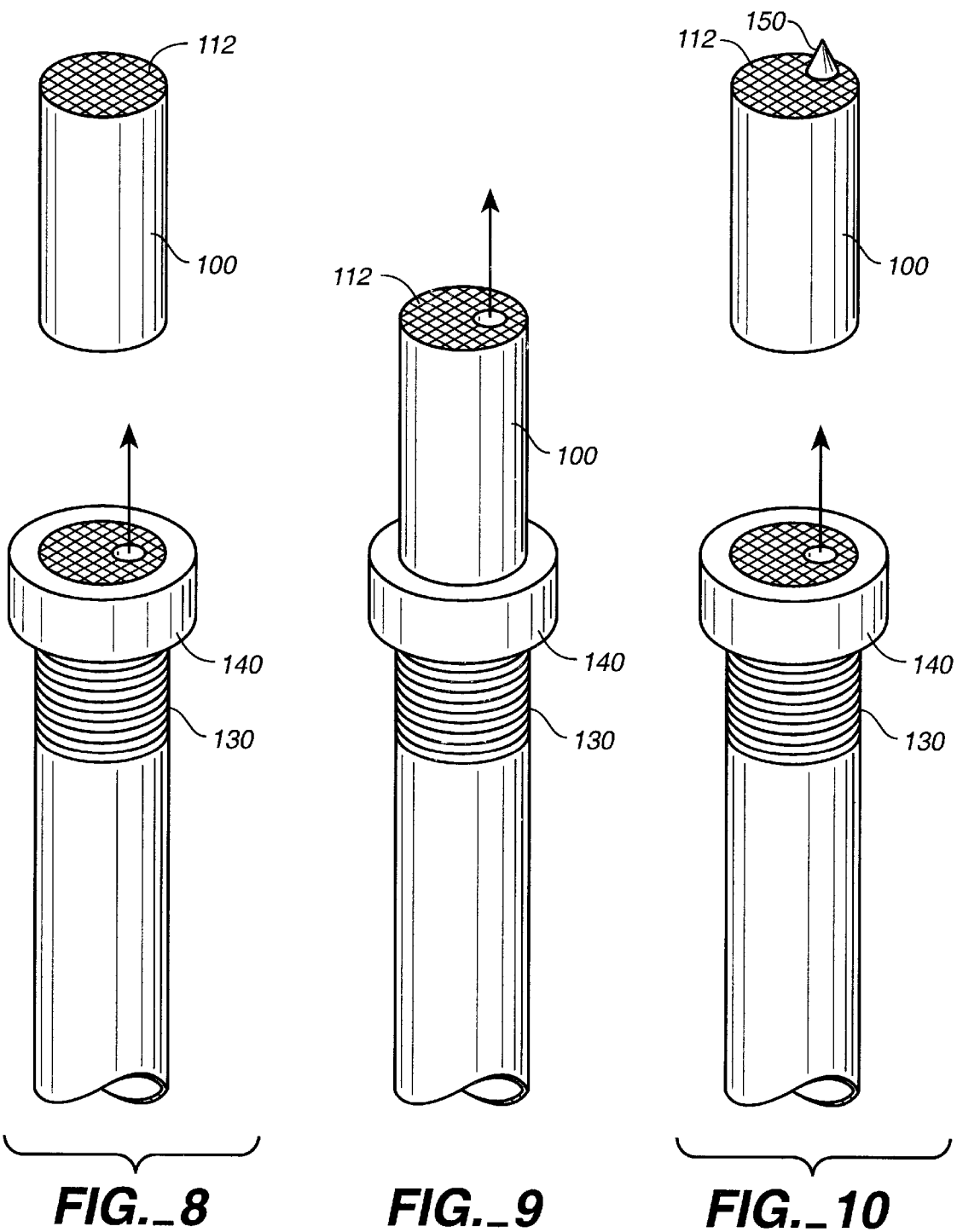
FIG._8  FIG._9  FIG._10

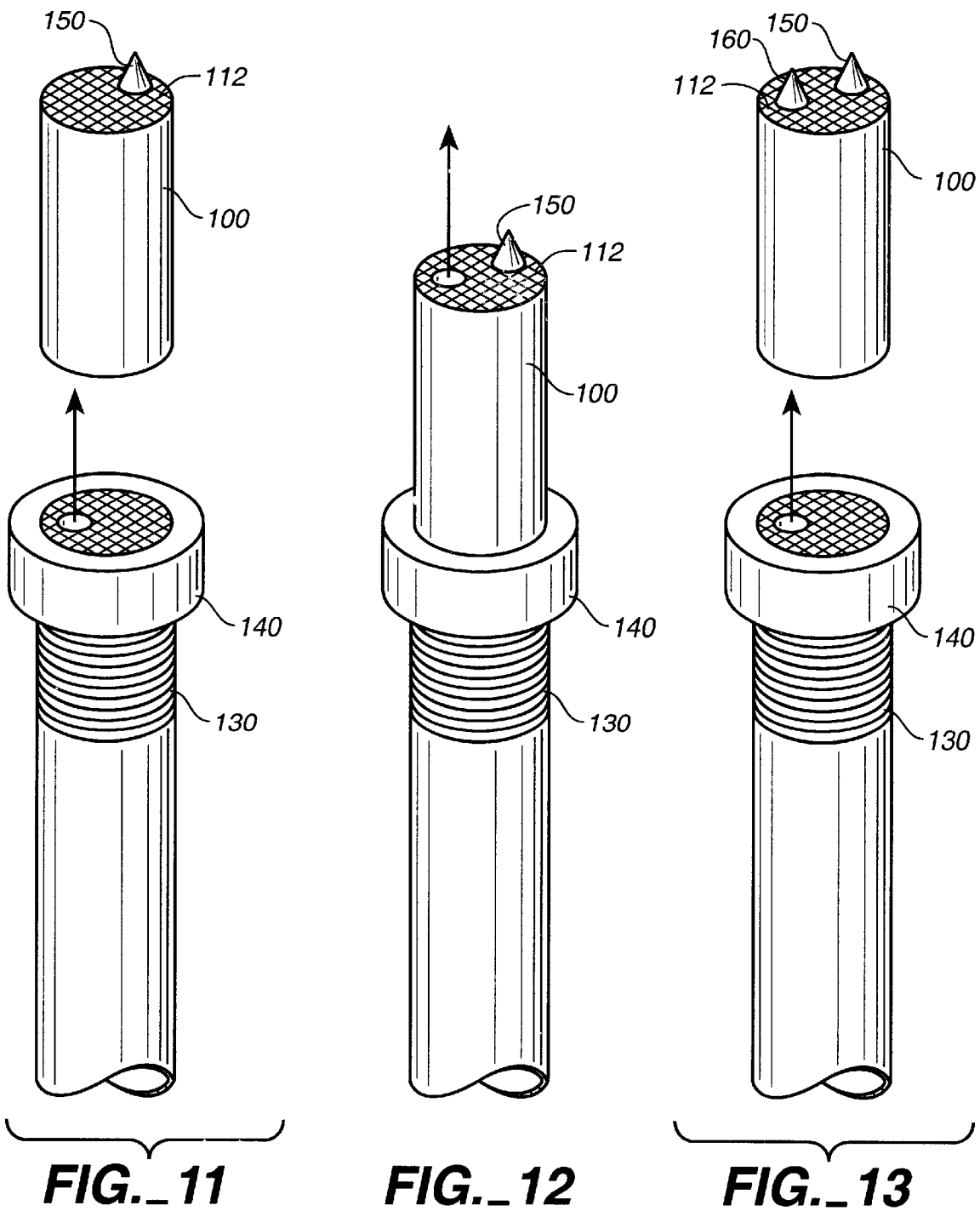
*FIG._11*  *FIG._12*  *FIG._13*

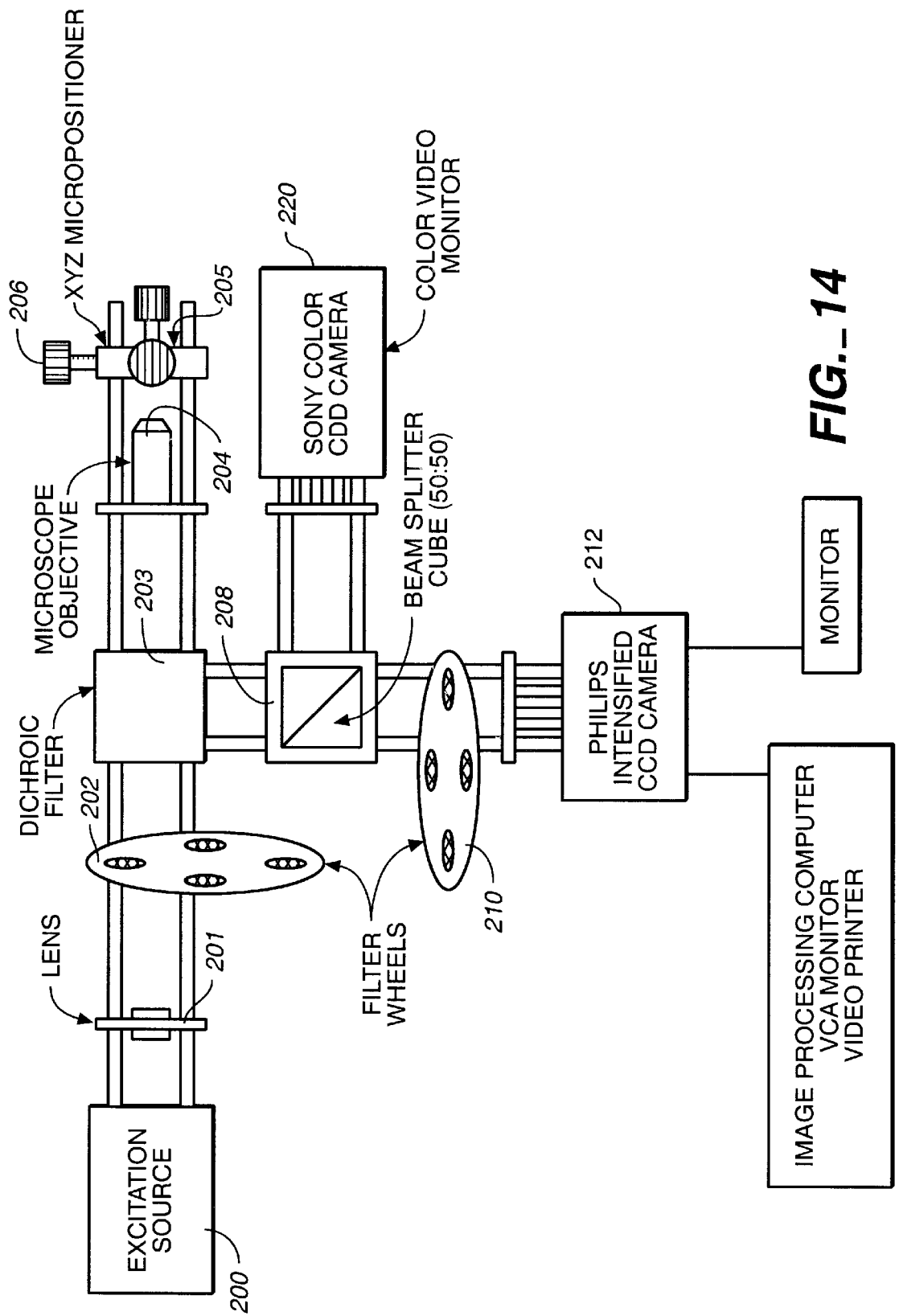
FIG._14

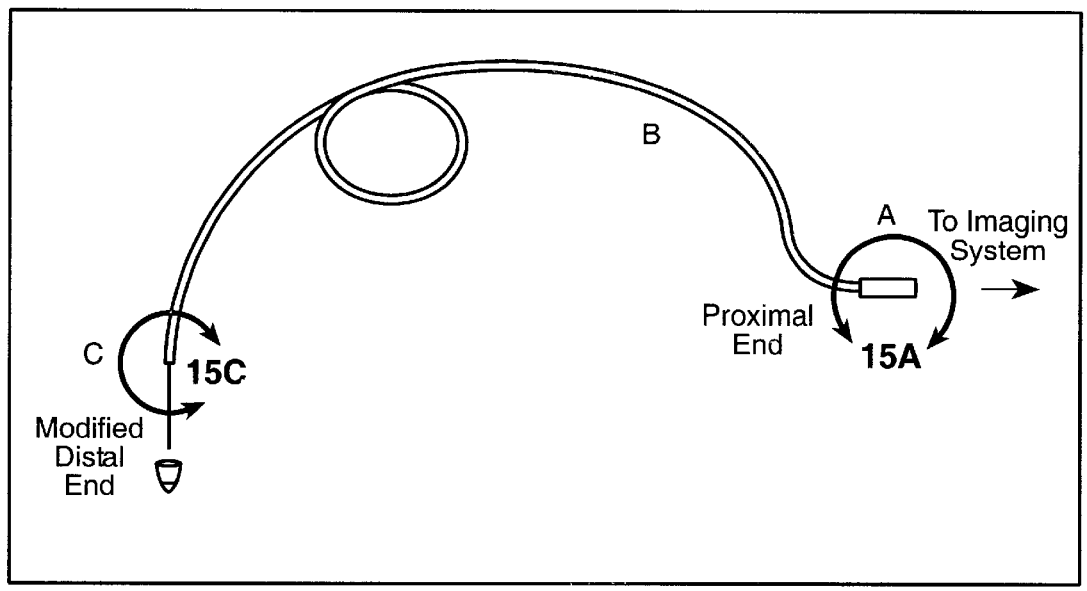
FIG._15B
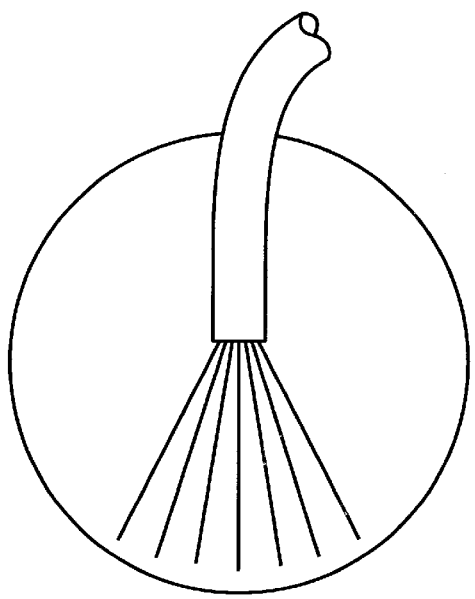
FIG._15C
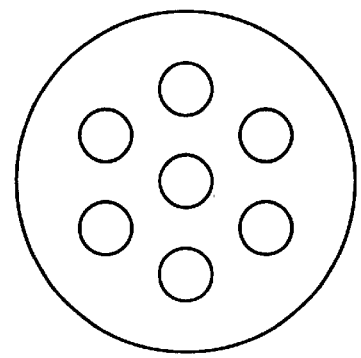
FIG._15A

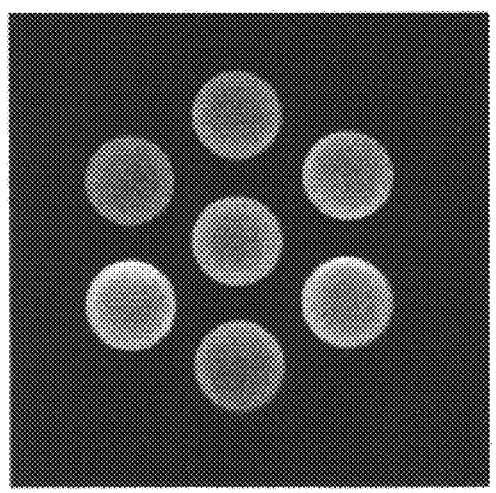 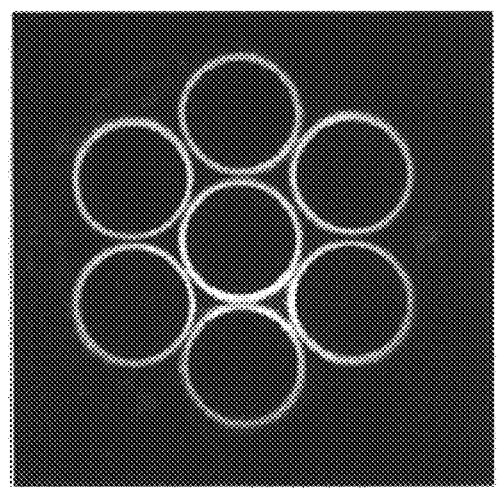
*FIG._16A*  *FIG._16B*
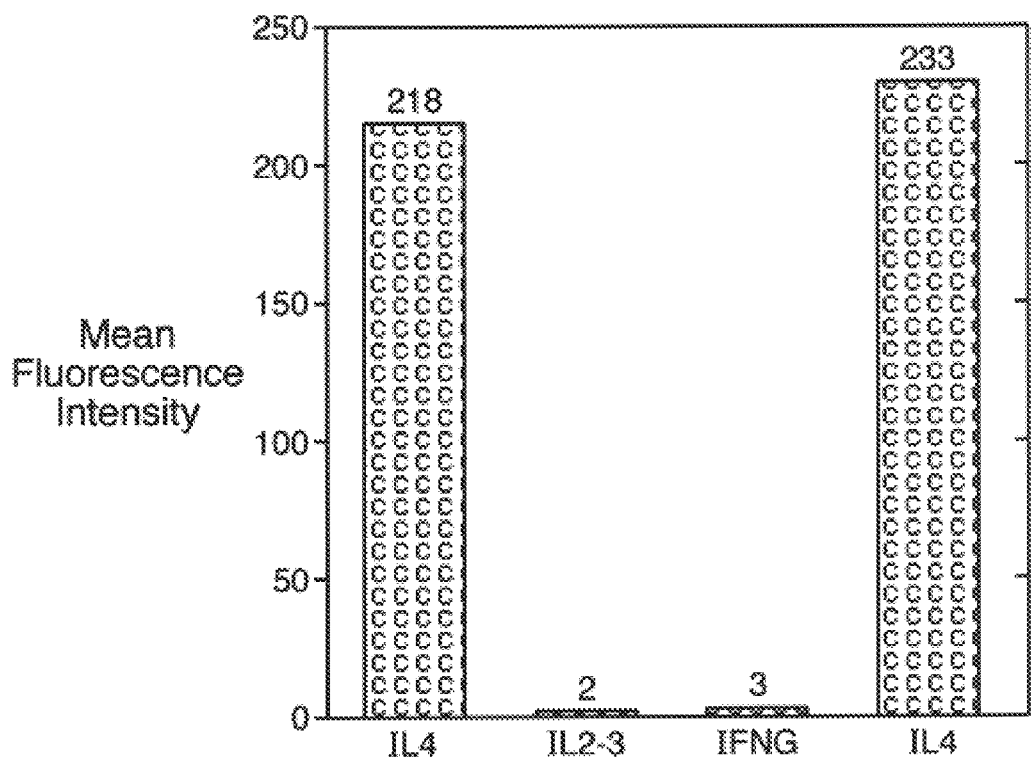
*FIG._17*

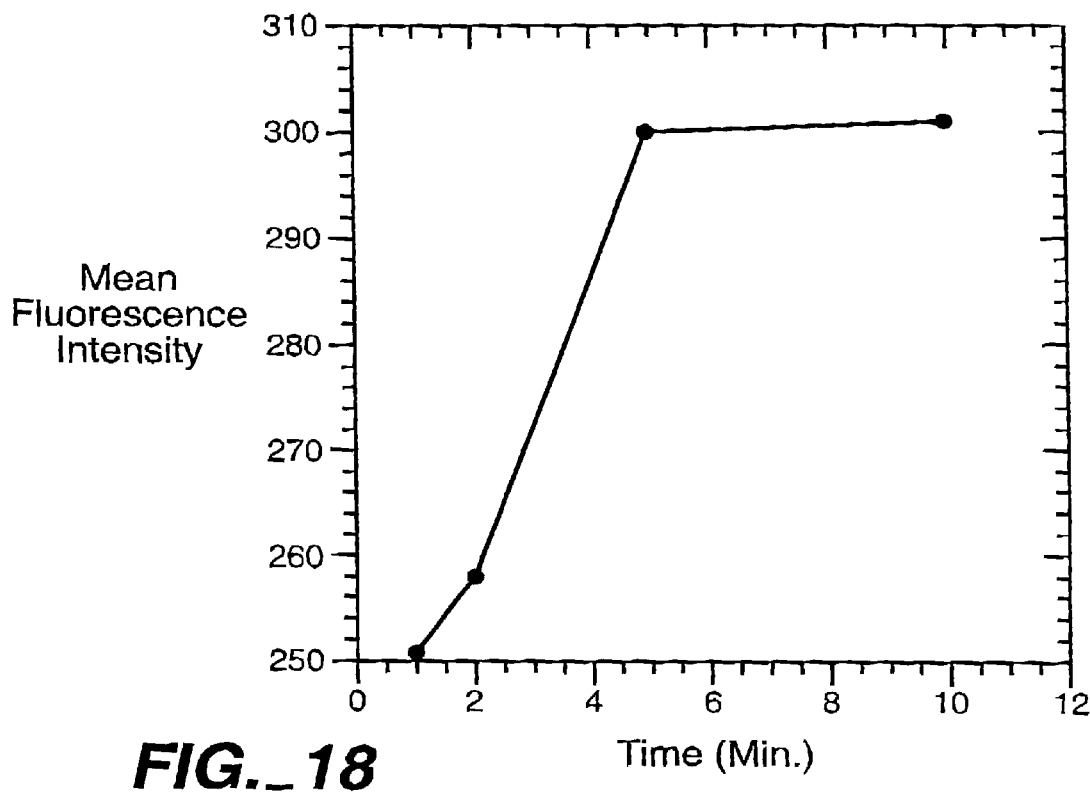
FIG._18
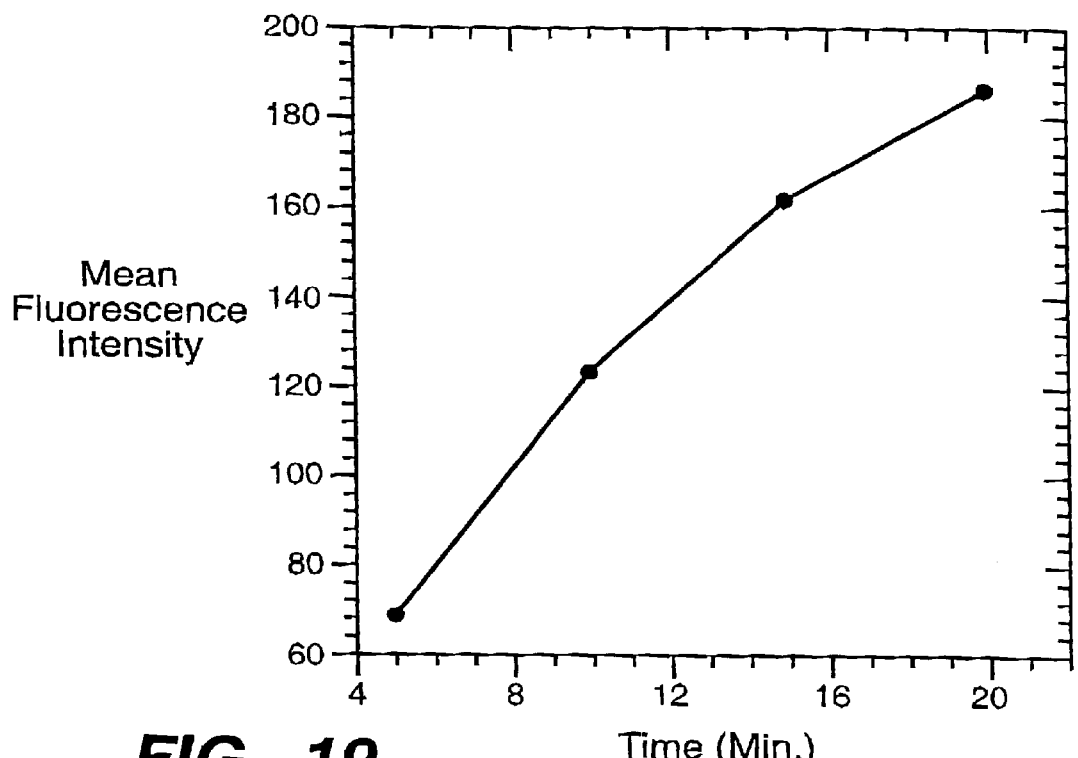
FIG._19

FIG._20A 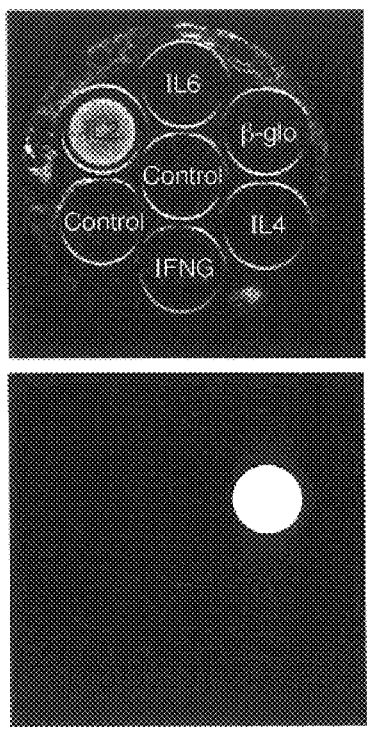 FIG._20B 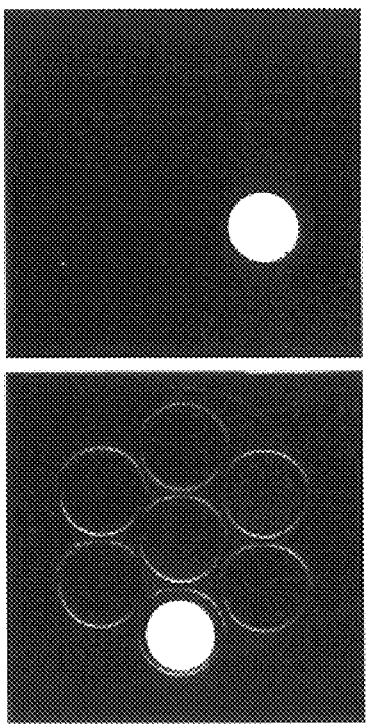 FIG._20C 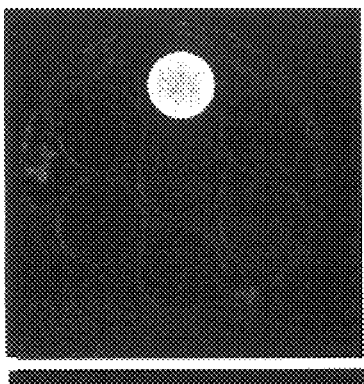
FIG._20D 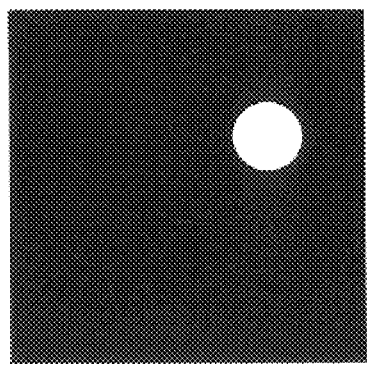 FIG._20E 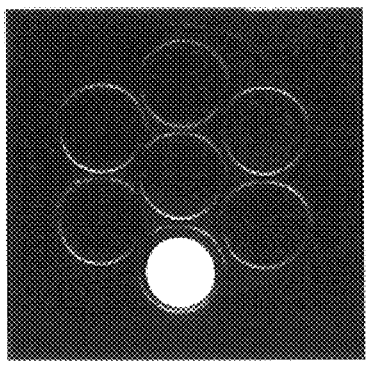 FIG._20F 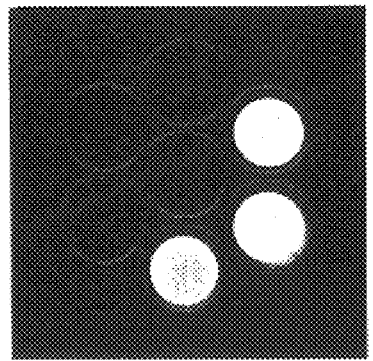

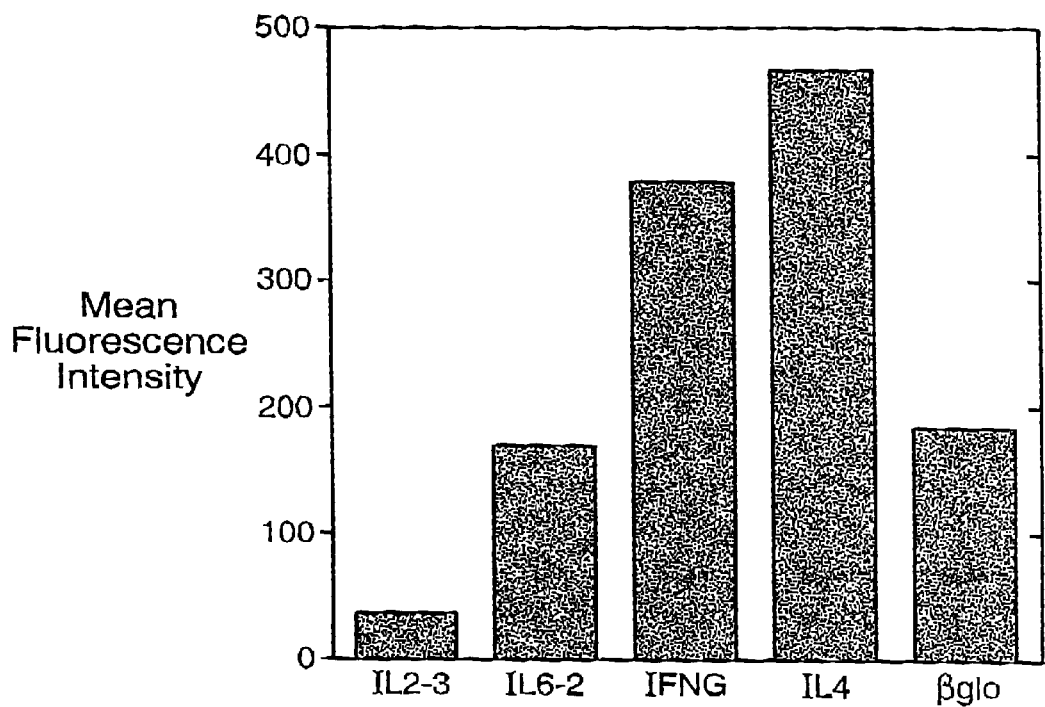
FIG._21
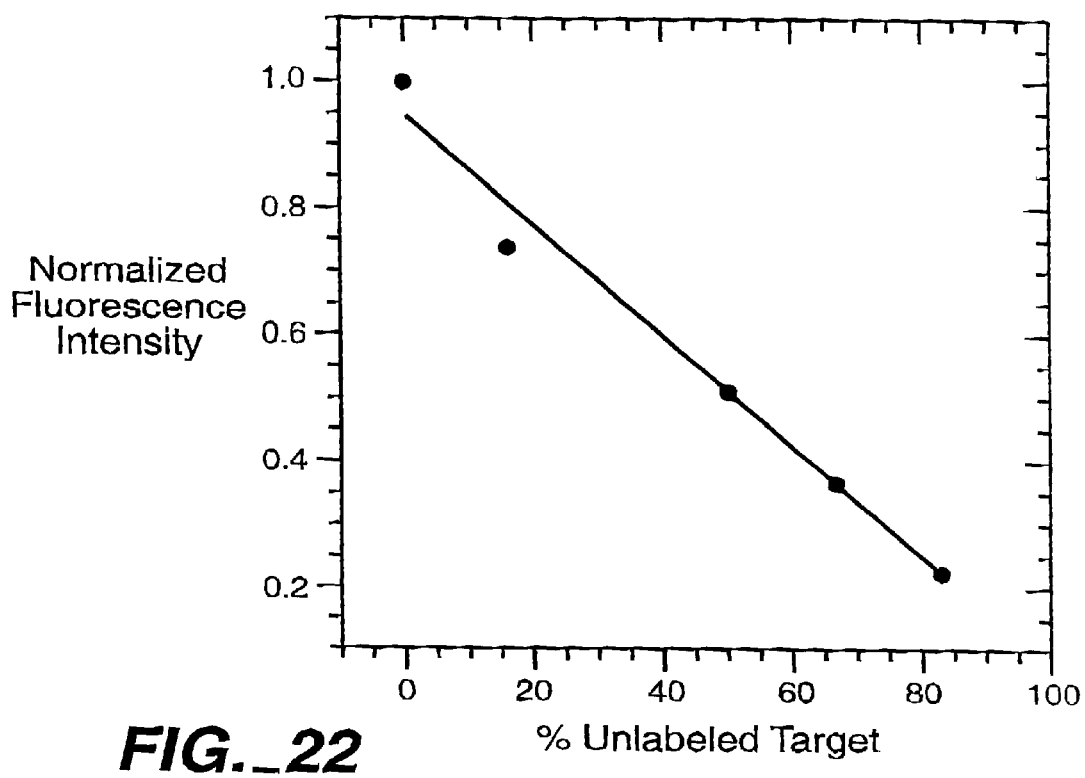
FIG._22

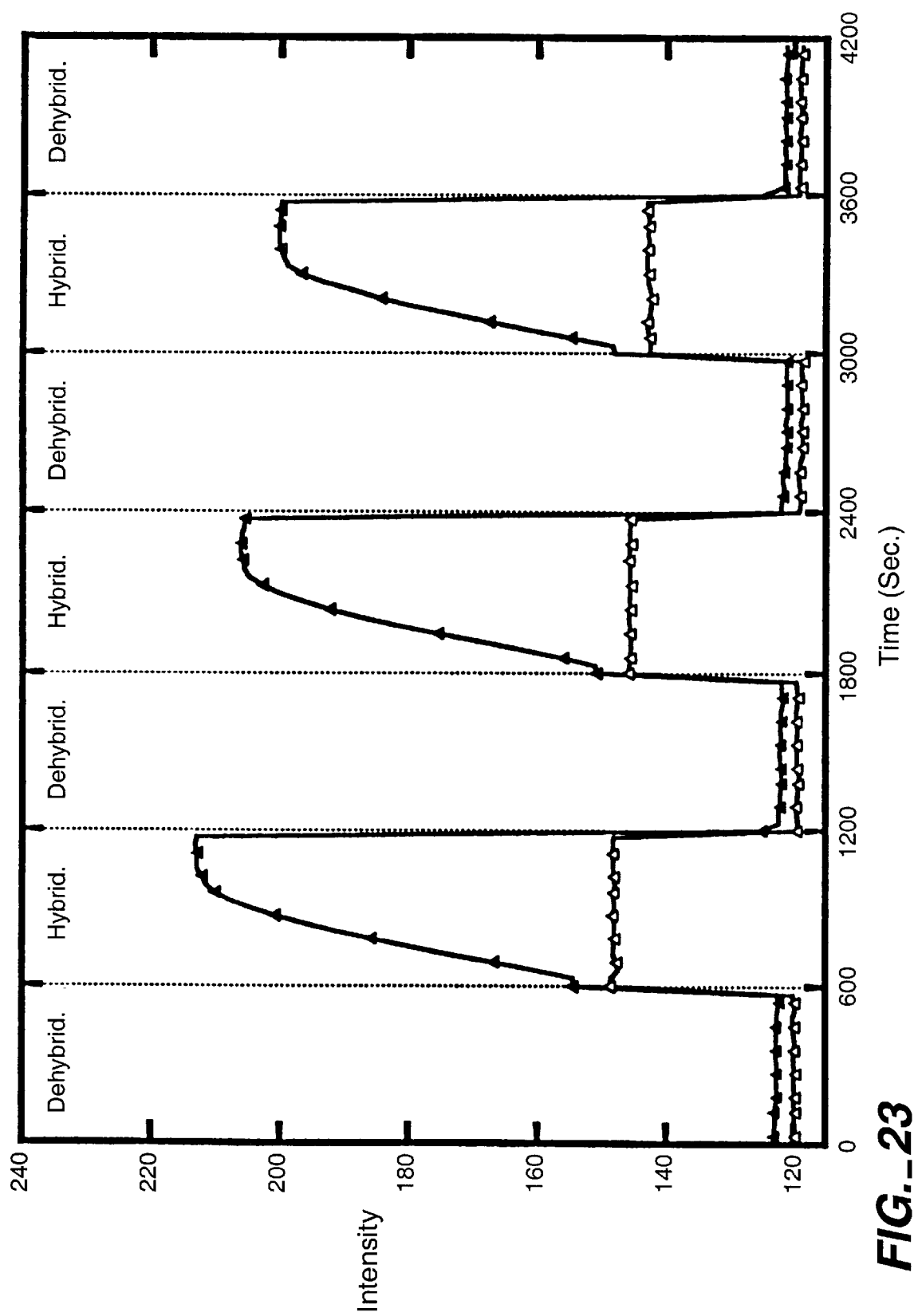
FIG._23

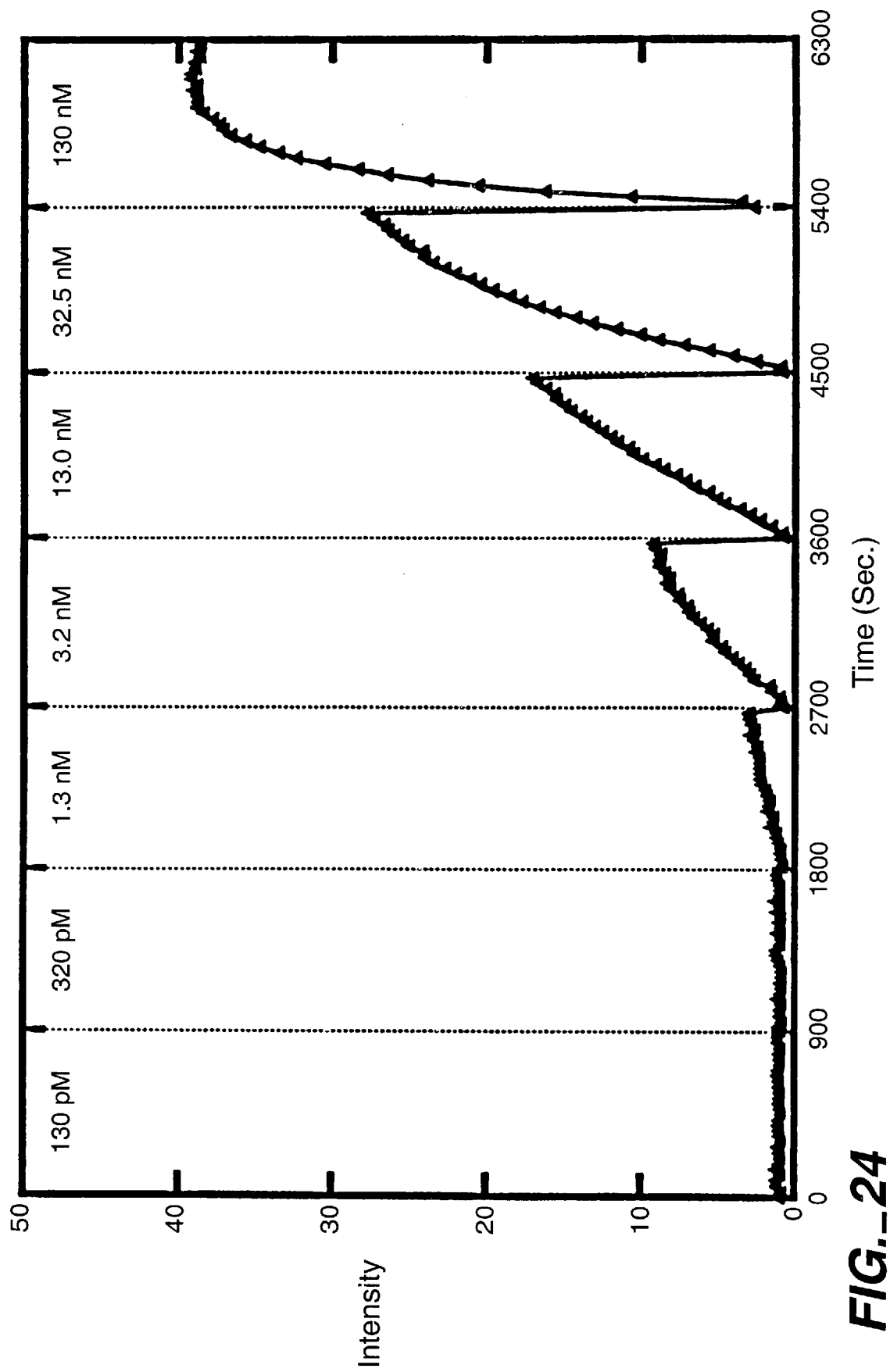
FIG._24

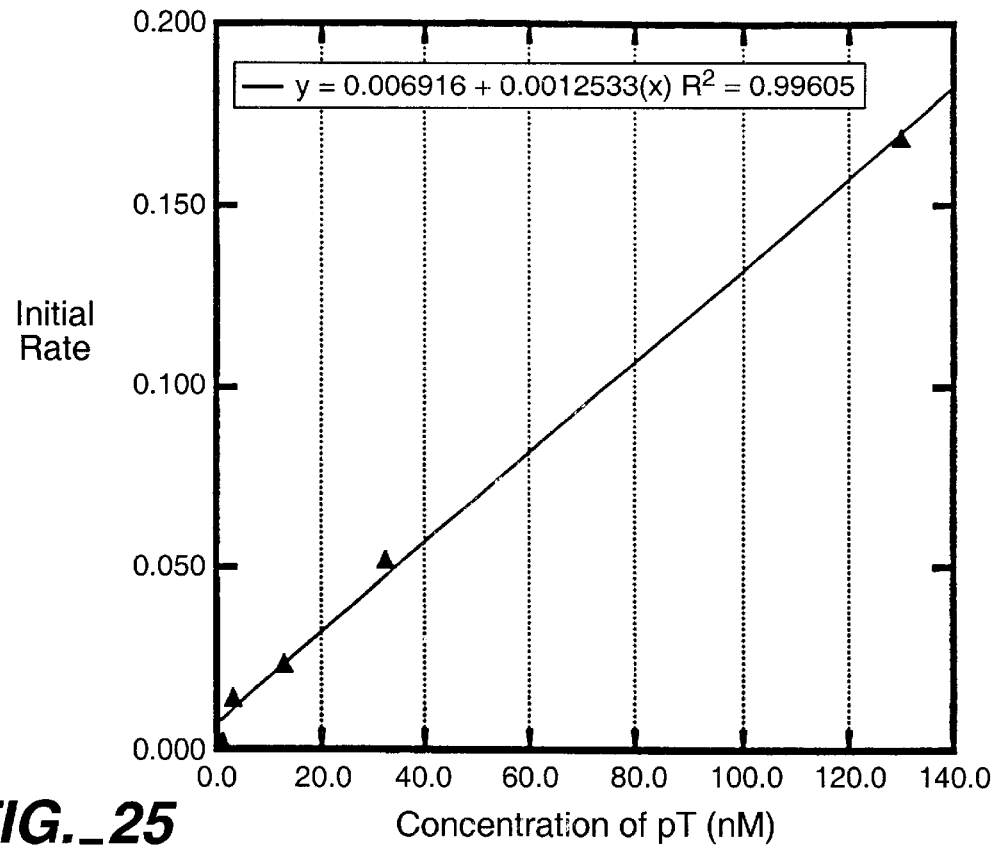
FIG._25
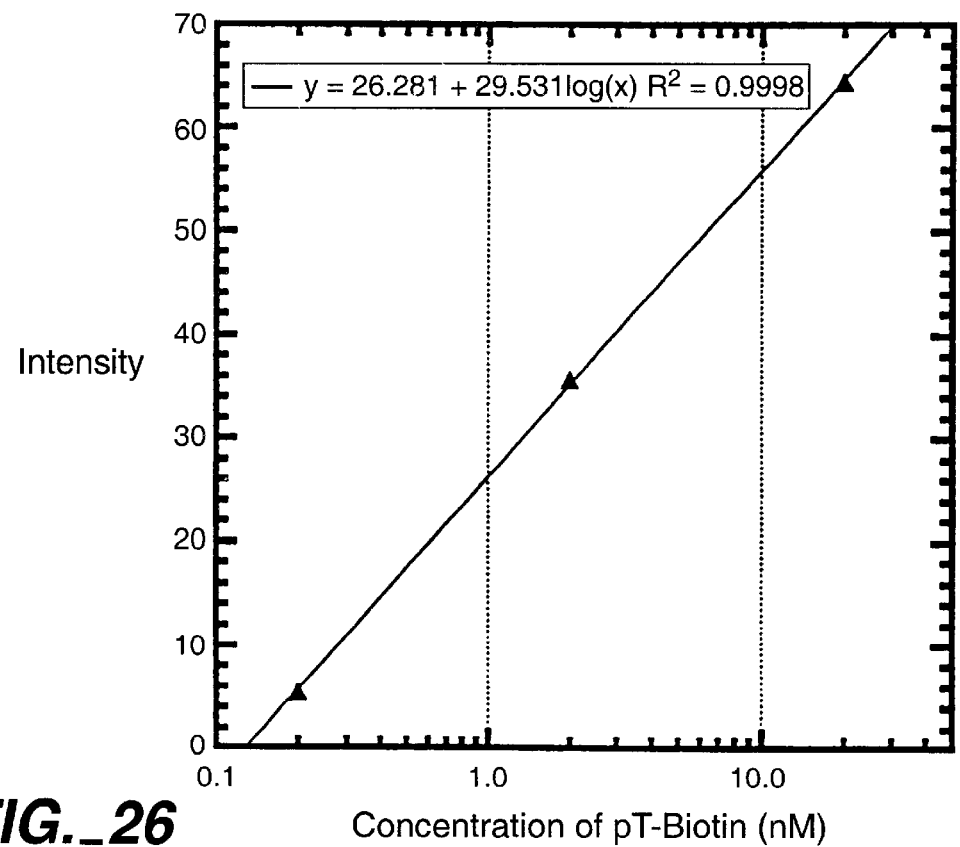
FIG._26

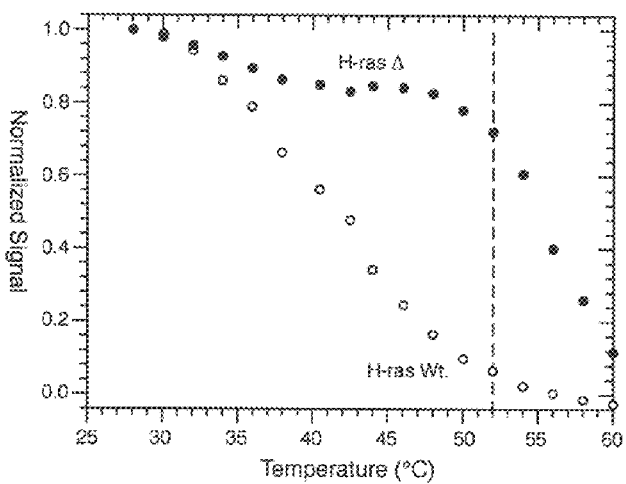
*FIG._27*
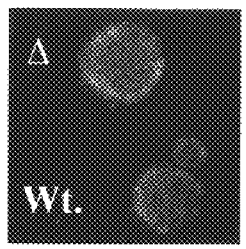
*FIG._28A*
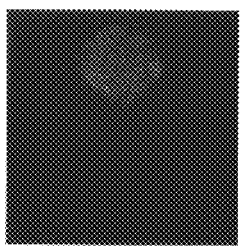
*FIG._28B*
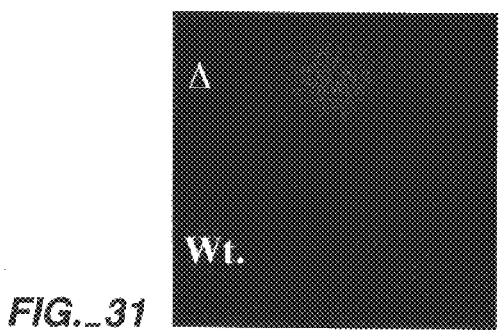
*FIG._31*

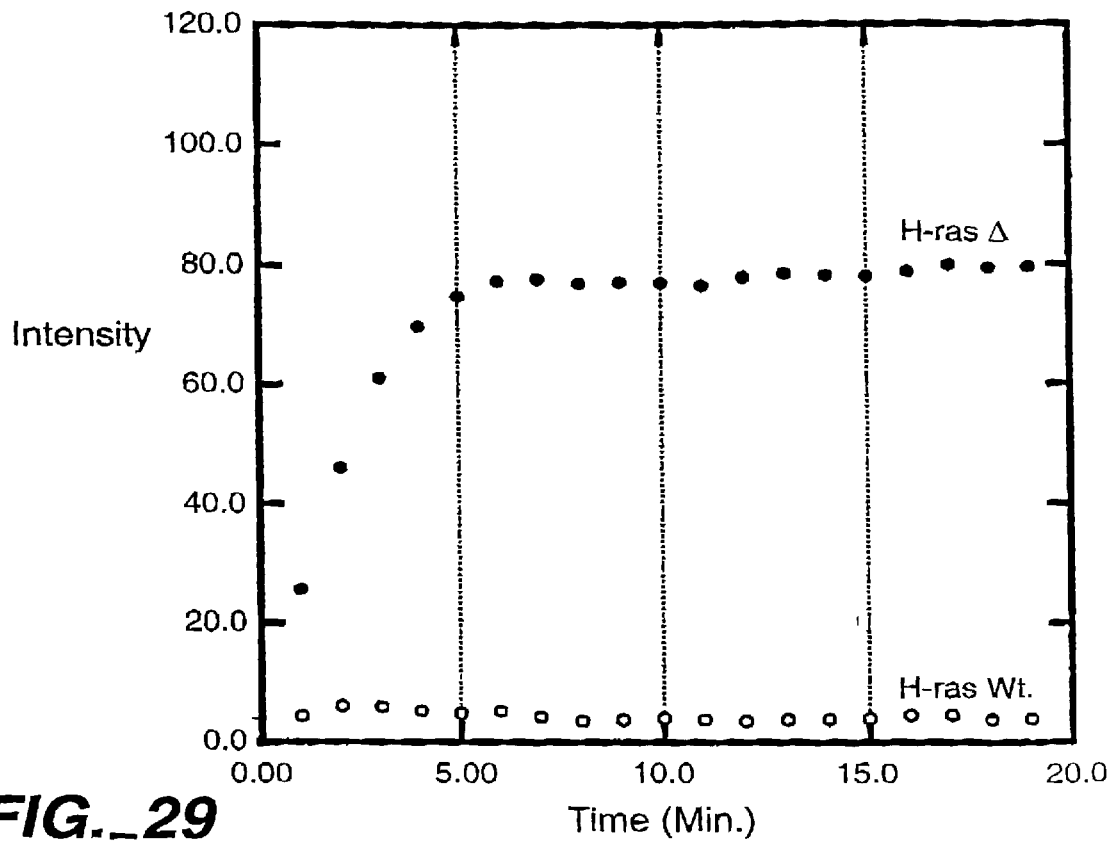
FIG._29
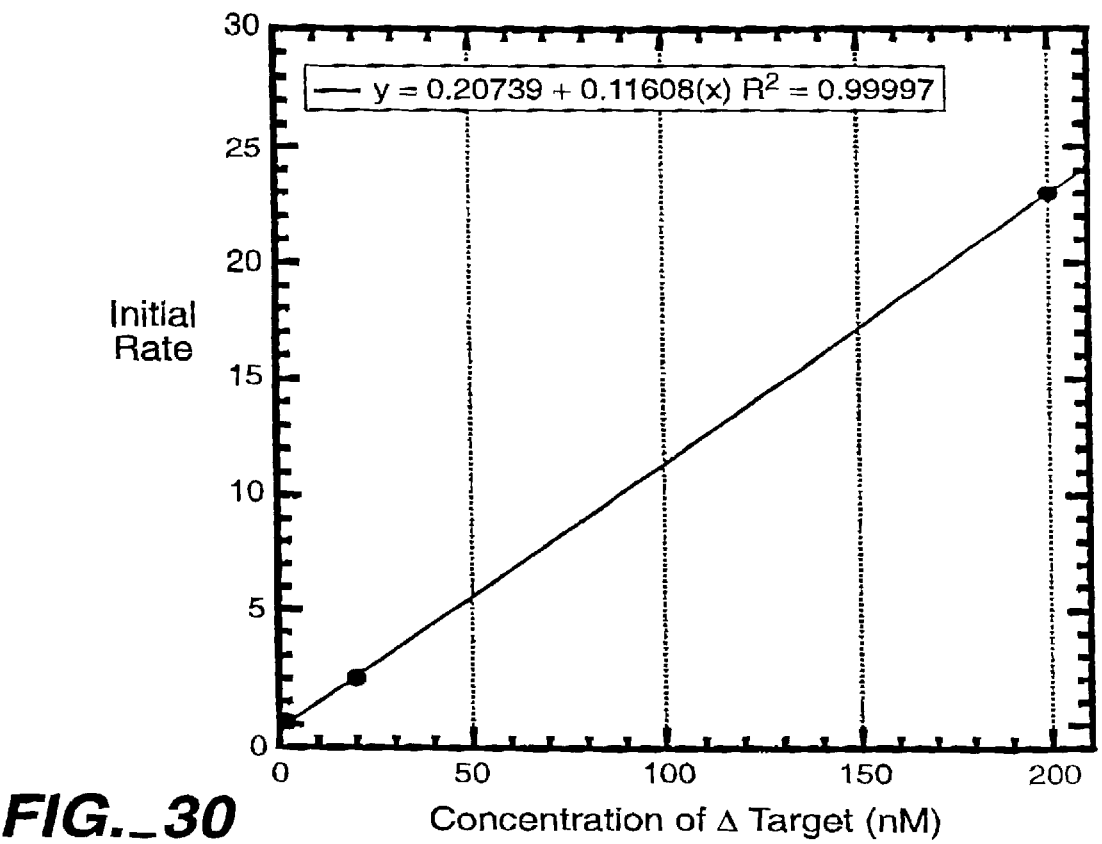
FIG._30

FIBER OPTIC BIOSENSOR FOR SELECTIVELY DETECTING OLIGONUCLEOTIDE SPECIES IN A MIXED FLUID SAMPLE

This application is a continuing application of co-pending application U.S. Ser. No. 08/851,203, filed May 5, 1997, the text of which is expressly incorporated by reference herein.

RESEARCH SUPPORT

This invention was made with government support under GM48142 awarded by the National Institutes of Health. The government has certain rights in the invention.

FIELD OF THE INVENTION

The present application is concerned generally with apparatus and methods for the analysis of genes and gene expression; and is particularly directed to the construction and use of a fiber optic biosensor able to detect selectively one or multiple nucleic acid oligonucleotide fragments concurrently.

BACKGROUND OF THE INVENTION

In less than twenty years, the field of molecular genetics, including the specialty of genetic engineering, has revolutionized the science of biology as a whole and is in the process of restructuring medicine in both diagnostic and therapeutic applications. Not only are individual genes now being isolated and characterized, but also extensive research studies as to how genes function and are regulated in-vivo are being actively pursued. Moreover, many techniques for manipulating and modifying genes have been reported and are today becoming widespread in use and diverse in application. Merely exemplifying the many authorative texts and published articles presently available in the literature regarding genes, gene manipulation and genetic analysis are the following: *Gene Probes for Bacteria* (Macario and De Macario, editors) Academic Press Inc. 1990; *Genetic Analysis, Principles Scope and Objectives* by John R. S. Fincham, Blackwell Science Ltd., 1994; *Recombinant DNA Methodology II* (Ray Wu, editor), Academic Press, 1995; *Molecular Cloning. A Laboratory Manual* (Maniatis, Fritsch, and Sambrook, editors), Cold Spring Harbor Laboratory, 1982; PCR (Polymerase Chain Reaction). (Newton and Graham, editors), Bios Scientific Publishers, 1994: and the many references individually cited within each of these publications.

Among the many innovative ideas and novel techniques generated by molecular genetic research studies has been the generation of nucleic acid probes for identifying the existence of specific genes, the products of gene expression, and the presence of mutations in one or more genes. By definition, a nucleic acid probe is a DNA or RNA oligonucleotide fragment or peptide nucleic acid (PNA) of known base sequence. Existing as a single-stranded segment of base codons, a nucleic acid probe which will bind to a complementary base sequence of nucleic acids which is the analyte of interest for any purpose. Thus, the oligonucleotide probe, via its selective binding capability, is employed to detect and identify individual gene fragments or nucleic acid sequences present in viruses, bacteria, and other cells serving as samples for scientific, research or medical interest.

In general, any DNA, RNA, or PNA sequential fragment (obtained from any source and regardless of whether the sequence is naturally occurring or synthetically prepared) must meet two essential criteria in order to be truly useful as an oligonucleotide probe. First, the oligonucleotide probe sequence must be as specific as possible for the intended complementary target sequence; and, preferably, bind exclusively with only the complementary target sequence with little or no cross-reaction. Secondly, the oligonucleotide probe must be able to distinguish among closely related nucleic acid base sequences having a substantial degree of homology as well as be able to bind selectively with varying types and sources of nucleic acid fragments having the complementary target sequence as part of its composition. Thus, the size or length of the oligonucleotide probe and the repetitive nature of or copy number for the complementary target sequence will meaningfully affect not only the specificity, but the sensitivity of the probe for detection purposes.

The technique employing an oligonucleotide probe for selective binding to a complementary target sequence is generally termed "hybridization". However, the development of hybridization based assays for the identification of specific genes and gene expression products has been severely limited to date because of major difficulties in: (a) isolating highly specific nucleic acid sequences for use as oligonucleotide probes: (b) developing assay formats that are sufficiently rapid and simple in order to identify even one complementary target sequence in a fluid mixture containing many varieties of different single-stranded oligonucleotides in admixture: and (c) devising non-radioactive detection systems that provide a desired level of sensitivity. Thus several types of DNA (or RNA, or PNA) hybridization assay formats have come into prevalent use.

Four hybridization assay formats are commonly employed today. Each of these hybridization detection formats suffers from relatively poor sensitivity, although various target sequence amplification techniques (such as PCR) have also been developed to reduce the severity of this problem. The four most commonly used types of hybridization assay formats are: the Southern blot technique; the dot or spot blot technique; in-situ hybridization; and sandwich hybridization assays. As with the selection of an appropriate oligonucleotide probe, the choice of a hybridization assay format often rests upon the degree of specificity and sensitivity that is required for the particular analysis; and upon the factors of speed, reliability, and ease of performance and interpretation of the assay result—which varies markedly among the different assay formats.

In Southern blot assays, specimen DNA is isolated and purified prior to restriction endonuclease digestion; followed by separation of the digestion products by electrophoresis on an agarose gel, denaturation of the DNA in the gel, and transfer of the denatured DNA fragments to a solid matrix such as a nitrocellulose membrane. The DNA bound to the solid matrix is then hybridized in the presence of radioactively labeled DNA targets to establish homology between the probe and target DNA. Hybridization of the targets to the probes is detected by autoradiography and often requires several days or weeks of exposure. This format is thus often too lengthy and cumbersome for routine or large-scale analyses of many specimens.

The dot-blot procedure also requires that specimen DNA be isolated and purified before being denatured and applied to a suitable solid matrix (such as nitrocellulose). Hybridization to the matrix-bound DNA is then performed using probe-specific targets. The hybridization of target DNA to the probe DNA is detected either by autoradiography or by visual inspection using non-radioactive detection procedures. The spot-blot assay format is similar except that specimens or specimen lysates are directly applied to the solid matrix without prior extraction of their DNA. Although this assay format allows many different samples to be processed at one time, these assays are often limited to high background noise that complicates the interpretation of results and is also subject to lengthy time of processing for each sample to be evaluated.

The in-situ hybridization technique intends that the DNA or RNA in the cells of a fixed tissue section or fixed culture cell be hybridized to DNA probes directly on a microscope slide. The results are determined by microscopy if non-radioactive detection systems are used and by autoradiography if radioisotopes are employed for the targets. This assay format can detect the presence of only a few copies of the target DNA sequence to be hybridized. This conventional in-situ hybridization assay is not suitable for screening large numbers of specimens due to the need to separate and remove extraneous cellular materials from the sample prior to addition of the labeled target.

Lastly, the sandwich hybridization assay requires that at least two different specific probes hybridize to the target DNA of interest, rather than just one probe alone. In this format, the first probe (the capture sequence) is bound to a solid support and is allowed to bind (capture) the specimen DNA. A second probe (the signaling probe) with a sequence that is adjacent or close to the capture sequence on the target DNA molecule is then allowed to hybridize to the support-bound target DNA. This signaling probe can be labeled with either radioactive or non-radioactive labels and the removal of non-specific cellular material in the first step of the procedure enhances the specificity of the hybridization assay by reducing the effects of contaminating tissue or debris.

More recently however, the value of using immobilized spatially distinguishable, hybridization probes for concurrent analyses of multiple gene sequences has been recognized and resulted in the development of miniaturized hybridization assays using solid matrix assays [Southern, E. M., Trends in Genetics 12: 110–115 (1956)]. Thus, hybridization using said matrix arrays have been performed on glass surfaces [Maskos, U. and E. M. Southern, Nuc. Acids. Res. 20: 1679–1684 (1992); Guo et al., Nuc. Acid. Res. 22: 5456–5465 (1994)]; on microtiter plates [Kalakowski et al., Anal. Chem. 68:1197–1200 (1996); Nikiforov et al., Nuc. Acids Res. 22: 4167–4175 (1994); Rasumussen et al., Anal. Biochem. 198: 138–142 (1991)]; on plastic sheets [Matson et. al., Anal. Biochem. 224: 110–116 (1995)]; on thin polymer gels [Khrapko et al., J. DNA Seq. Map 1:375–388 (1991)]: and using semiconductor devices [Eggers et al, Bio Techniques 17: 516–524 (1994); Kreiner, T, Am. Lab.: 39–43 (1996)]. In addition, the desire for using non-radioactive means for detection have caused a surge of interest in means for detection of hybridization on solid matrix supports which employ fluorescence [Kumke et. al., Anal. Chem. 67: 3945–3951 (1995); Piunno et. al. Anal. Chim. Acta. 288: 205–214 (1994)]; chemiluminescence [Ito et. al. J. Neurosci. Methods 59: 265–271 (1995); Nguyen et. al., Biosen. Bioelectron. 7: 487–493 (1995)] evanescent wave technology [Graham et. al., Biosen. Bioelectron. 7: 487–493 (1992): Strachan et. al Lett. Aor:. Microbiol. 21:5–9 (1995). Watts et. alAnal. Chem. 67: 4283–4289 (1995)]: confocal microscopy [Fodor et. al. Nature (London) 364: 555–556 (1993)]: light scattering [Stimpson et. al., Proc. Natl. Acad. Sci. USA 92: 6379–6383 (1995)]: electrochemistry [Millard et. alAnal. Chem. 66: 2943–2948 (1994): Pandey et. al. Anal. Chem. 66:1236–1241 (1954): Hashimoto et. al., Anal. Chim. Acta. 286:219–224 (1994)]: and surface resonance phenomena [Yamaguchi et. al, Anal. Chem. 65: 1925–1927 (1993)].

Despite these recent innovations using probes immobilized on solid matrix arrays the major obstacles and limitations of hybridization methods generally continue to restrict and contain the currently available techniques and formats. These demands and limitations include a requirement for a large sample volume; an inability to perform multiple analyses concurrently in real time; a requirement for a relatively high concentration of target DNA (the complementary target sequence) in the fluid sample; an inability to detect multiple species concurrently; relatively slow kinetics for hybridization to occur between the target sequences and the immobilized probes within the assay format; and a dependence upon lengthy assays. Moreover, despite the use of new in-vitro amplification techniques such as the polymerase chain reaction procedure, the problems of assay sensitivity, lengthy times for analysis, the quantum of background signal noise, and the inability to detect more than one target nucleic acid sequence at a time remain as recurring handicaps and continuing obstacles for each of these techniques. It will be recognized and appreciated by persons working in this field today, therefore, that the development of a unique biosensor which overcomes and eliminates most, if not all of these major limitations and procedural hindrances would be seen as a major advance and unforeseen improvement in this art.

SUMMARY OF THE INVENTION

The present invention provides optical sensors for detecting nucleic acids in a fluid sample. The sensors comprise a preformed, unitary fiber optic array comprising a plurality of optical fiber strands, the strands being disposed co-axially and joined along their lengths. The fiber optic array has a proximal and distal end, and each of the ends are formed by multiple strand faces of the strands. At least one of the array ends presentes a discrete fiber optic array surface for introduction and conveyance of light energy. The array further comprises at least a first and a second nucleic acid attached to a first and second portion, respectively, of the distal array end. The first nucleic acid is optically coupled to and in optical communication with a first of the multiple end faces at the distal array end, and the second nucleic acid is optically coupled to and in optical communication with a second of the multiple end faces at the distal array end.

In an additional aspect, the present invention provides methods of making a fiber optic sensor. The method comprises providing a preformed, unitary fiber optic array as outlined above, and contacting at least a first nucleic acid and a photoactivatable compound with at least a first distall optic fiber strand end face, such that the first nucleic acid is attached to the end face by introducing light energy to the first optic fiber strand.

In a further aspect, the invention provides methods of detecting at least one target sequence in a fluid sample. The method comprises providing a preformed, unitary fiber optic array as outlined herein, and contacting the distal end of the array with the sample. The presence or absence of the target sequence is then detected.

BRIEF DESCRIPTION OF THE FIGURES

The present invention may be more easily understood and better appreciated when taken in conjunction with the accompanying drawing in which:

FIG. 1 is an overhead view of an individually clad optical fiber strand:

FIGS. 2A and 2B are views of the proximal and distal surfaces of the fiber optical strand of FIG. 1:

FIGS. 3A and 3B are alternative constructions of the optical end surface for the optical fiber strand of FIG. 1;

FIG. 4 is an overhead view of a preformed, unitary fiber optic array using the optical fiber strand of FIG. 1;

FIG. 5 is a view of the intended distal array end surface of the unitary fiber optic array of FIG. 4;

FIG. 6 is a view of the intended proximal array end surface of the unitary fiber optic array of FIG. 4;

FIG. 7 is a frontal view of an illumination source able to provide light energy at precise spatial positions concurrently;

FIGS. 8–13 illustrate the manipulative steps performed during the disposition of oligonucleotide probes at precise spatial positions on the distal array end surface of FIG. 6.

FIG. 14 is a schematic diagram of the apparatus comprising the biosensor;

FIG. 15 is a schematic diagram of a fiber optic biosensor detection apparatus and system;

FIGS. 16A and 16B are white light and background fluorescent images viewed through the proximal end of the biosensor apparatus;

FIG. 17 is a graph showing the background-subtracted mean fluorescence intensities obtained with fixed IL4 probes on the distal end of the biosensor;

FIG. 18 is a graph showing the plot of background-subtracted mean fluorescence as a function of time using a sensor having a β-glo probe and a 1.0 uM β-glo target solution;

FIG. 19 is a graph showing the plot of background-subtracted mean fluorescence as a function of time using a sensor having a β-glo probe and an 0.1 mM, β-glo target solution;

FIGS. 20A–20F are fluorescent images from a biosensor apparatus after immersion in a IL2 target, an IL4 target, an IL6 target, a β-glo target, an IFNG target, an IL4 and IFNG and β-glo targets;

FIG. 21 is a graph illustrating the background-subtracted mean fluorescence signals as a function of the probe/target pair of FIG. 20;

FIG. 22 is a graph showing the plot of hybridization competition between labeled and unlabeled formats of the same target nucleic acid sequence;

FIG. 23 is a graph showing the fluorescence intensity of the poly(dA) matrix upon repeated hybridization to and dehybridization from a poly(dT)-FITC target;

FIG. 24 is a graph showing the fluorescence intensity of a poly(dA)/acrylamide biosensor to varying concentrations of poly(dT)-FITC;

FIG. 25 is a graph showing the calibration curve of the data of FIG. 23;

FIG. 26 is a graph showing the calibration curve of a poly(dA) matrix biosensor after in-situ hybridization with a poly(dT)-biotin target;

FIG. 27 is a graph showing the melting curves of a DNA biosensor after hybridization to a Δ target at 28° C.

FIGS. 28A and 28B are fluorescent images from the DNA biosensor apparatus after in-situ hybridization with a Δ-FITC target at 28° C. and 50° C. respectively;

FIG. 29 is a graph showing the fluorescence intensity over time for in-situ hybridization of a 196 nM Δ target to a H-ras wt./H-ras Δ matrix biosensor;

FIG. 30 is a graph showing the calibration of a DNA biosensor to a Δ-FITC target at 54° C.; and FIG. 31 is a fluorescence image from a DNA biosensor apparatus after a 20 minute hybridization time to a biotinylated Δ PCR amplicon at 54° C., followed by a 5 minute labeling reaction with streptavidin-FITC.

DETAILED DESCRIPTION OF THE INVENTION

The present invention is directed to a fiber optic biosensor comprising a preformed, unitary array of fibers, with oligonucleotide probes immobilized at individual and differing spatial positions on the distal end surface. The immobilized oligonucleotide probe(s) generally do not bear any identifying label of any kind. Rather, it is the incoming target nucleic acid that bears the label. That is, when the distal array end surface supporting the immobilized probes are placed into reactive contact with a fluid sample containing at least one substantially complementary target nucleic acid bearing a joined identifying label, a hybridization complex is formed between the surface probe at a particular spatial position and the labeled target sequence. The presence of the target sequence can be detected and monitored by observing the fluorescence or reflected color of the joined identifying label that accompanied or is the consequence of hybridization at that specific spatial position. Equally important, because the hybridization can be relatively specific between the oligonucleotide base sequence of the spatially immobilized probe with a substantially complementary target base sequence, the detection of fluorescent, luminescent, transmitted, emitted, scattered or reflected light energy from the joined label at a predetermined spatial position on the distal end surface will demonstrate and evidence the occurrence of a specific and selective in-situ hybridization.

A number of different major advantages and unique capabilities are thus provided by the biosensor comprising the present invention. The unitary fiber optic array format provides collectives of multiple and different fixed sets of specie-specific probes, each set of fixed probes being collectively suitable for selective in-situ hybridization with a different mobile substantially complementary oligonucleotide target sequence. The unitary fiber optic array format and the bundled array of fibers format are thus able to detect multiple and diverse types of mobile oligonucleotide target species simultaneously or concurrently in one sample and a single test. Thus, due to the high density available in preformed unitary arrays, large numbers of reactions, i.e. a plurality of sequences, can be simultaneously monitored.

In addition, the present invention provides a biosensor which is extraordinarily rapid in providing evaluations and results based on in-situ hybridization reactions. Typically the biosensor will provide optical detection of a labeled complementary target specie in a fluid sample in less than ten (10) minutes time; and depending on the chosen components of the detection system, may provide optical detection of multiple target species concurrently or simultaneously within the same time duration, approximately ten minutes or less. The present invention thus provides a speed of detection which is unmatched by any previously known format or conventional technique.

Furthermore, the present invention provides an extremely high level of sensitivity for in-situ hybridization reaction. As the experimental data provided hereinafter reveals even a simple embodiment of the biosensor and its supporting, apparatus can optically detect 10 nM of a target oligonucleotide segment via the spectral characteristics of a joined identifying label. The apparatus and method of optical detection yields very little background signal as noise; and it is expected that as little as 0.01–0.1 nM will be detectable under optimum operating conditions. Accordingly, the traditional requirement for high concentrations of nucleic acid test sample in order that an accurate and reliable measurement be made is no longer necessary or required. Also, the absolute amounts of nucleic acid needed for detection are small due to the extremely small size of the sensor.

The present invention will provide high specificity of in-situ hybridization reactions in a fluid sample when used at ambient room temperatures generally, or at elevated temperatures. No special or unique environmental considerations or demands are necessary in order to use the present invention; to the contrary, the sole requirement is that the distal end surface bearing the specie-specific fixed probes be placed in reactive contact with a fluid sample suspected of carrying the complementary target base sequence.

The present invention requires only a very small fluid sample volume in order for optical determinations to be made and accurate results to be obtained. If necessary, a few nanoliters of fluid may be employed for detection purposes. It is generally desirable however, that a 1–2 microliter volume or greater be employed as the fluid sample. This low volume feature for the fluid sample may be maintained so long as there is sufficient liquid volume to cover the distal end surface effectively such that the fixed probe(s) immobilized on the distal surface may come into reactive contact with the contents of the fluid sample itself. If this minimal requirement is met and satisfied by the user, the true volume of the fluid sample is irrelevant and inconsequential.

A further benefit of the present invention is that it allows the user to monitor the hybridization process over time in-situ without physical separation of the apparatus from the fluid sample undergoing evaluation. Thus, assuming the user employs a very rapid reaction time for analysis (less than 10 minutes), continuous observation and optical detection of the ongoing hybridization process over the 10 minutes can be made for one or for all of the differing spatial positions for the fixed probes immobilized on the distal end surface. Thus as hybridization occurs at each fixed probe location on the end surface, the presence of a bound label joined directly or indirectly to the complementary target specie will be detected via the spectral characteristics of the light energy absorbing dye employed as an identifying label. The user may thus monitor the ongoing reaction in real time as it actually proceeds in-situ; and may determine even more quickly whether or not the complementary target specie does in fact exist within that fluid sample.

Finally, the biosensor of the present invention allows the user not only to detect rapidly the presence of the complementary target base segment in a fluid sample, but also permits the user to quantify in proportional degree the concentration of the complementary target specie actually present in the fluid sample volume. A semi-quantitative estimate is based on a calibrated detection of the signal intensity emanating from the fixed probes undergoing in-situ hybridization with the fluid sample. In addition, a competitive assay in which a fixed amount of added labeled target sequence is displaced proportionately by an unknown quantity of unlabeled target in a test sample will also provide quantitative results. A quantitative estimate which is both reliable and reproducible is rarely otherwise available without much more rigorous experiments and analytical test conditions.

Accordingly, the present invention provides biosensors comprising preformed, unitary fiber optic arrays. By "array" herein is meant a plurality of nucleic acids in an array format; the size of the array will depend on the composition and end use of the array. Arrays containing from about 2 different nucleic acid probes to many millions can be made, with very large fiber optic arrays being possible. Generally, the array will comprise from two to as many as a billion or more, depending on the end use of the array, thus very high density, high density, moderate density, low density and very low density arrays may be made. By "preformed unitary fiber optic array" herein is meant a fiber optic array of discrete individual fiber optic strands that are co-axially disposed and joined along their lengths. The arrangement of individual strands in the unitary array may be uniformly aligned, randomly aligned, semi-randomly aligned, coherent, for example as in an imaging fiber, or incoherent. The individual fiber strands may be individually clad or, alternatively, unclad. It is important to note, however, that a preformed unitary array is distinguished from other fiber optic array formats, such bundles of individual fibers, in that the individual fiber strands in the unitary array are not individually physically manipulatable; that is, one strand generally cannot be physically separated at any point along its length from another fiber strand.

A typical optical fiber strand is illustrated by FIGS. 1 and 2A and 2B. As seen therein, an individual optical fiber strand 10 is comprised of a single optical fiber 12 having a rod-like shaft 14 and two fiber ends 16, 18, each of which provides a substantially planar end surface. The intended distal surface 20 at the fiber end 16 is illustrated by FIG. 2A while the intended proximal surface 22 at the fiber end 18 is illustrated within FIG. 2B. It will be recognized and appreciated that the terms "proximal" and "distal" are relative and interchangeable until the strand is ultimately positioned in an apparatus. The optical fiber 12 is composed typically of glass or plastic: and is a flexible rod able to convey light energy introduced at either of its ends 16 and 18. Such optical fibers 12 are conventionally known and commercially available. Alternatively, the user may himself prepare individual optical fibers in accordance with the practices and techniques reported in the scientific and industrial literature. Accordingly, the optical fiber 12 is deemed to be conventionally known and available as such.

It will be appreciated that FIGS. 1–2 are illustrations in which the features have been purposely magnified and exaggerated beyond their normal scale in order to provide both clarity and extreme detail. Typically, a conventional optical fiber has a cross section diameter of 5–500 micrometers, although fibers with substantially smaller, submicron diameters are also known. Such fibers are routinely employed in lengths ranging between millimeters, centimeters and meters (in the laboratory) to kilometers (in field telecommunications). Moreover, although the optical fiber 12 is illustrated via FIGS. 1–2 as a cylindrical extended rod having substantially circular proximal and distal end surfaces, there is no requirement or demand that this specific configuration be maintained. To the contrary, the optical fiber may be polygonal or asymmetrically shaped along its length; provided with special patterns and shapes at the proximal and/or distal faces; and need not present an end surface which is substantially planar. Nevertheless, for best efforts, it is presently believed that the substantially cylindrical rod-like optical fiber having planar end surfaces is most desirable.

Each optical fiber 12 is desirably, but not necessarily, individually clad axially along its length by cladding 26. This cladding 26 is composed of any material with a lower refractive index than the fiber core and prevents the transmission of light energy photons from the optical fiber 12 to the external environment. The cladding material 26 may thus be composed of a variety of radically different chemical formulations including various glasses, silicones, plastics platings and shielding matter of diverse chemical composition and formulation. The use of a cladding material generally reduces optical signal losses during transmission and eliminates noise and cross-talk between adjacent fibers. The cladding also prevents optical transmission losses to the external environment. Accordingly, the potential for optical signal loss, distortion, or other optical error is minimized and reduced. For these reasons, the individually clad optical fiber mode of construction is preferable to the use of bare optical fiber strands in order to improve signal to noise during optical transmission. The manner in which the optical fiber 12 is clad is also inconsequential and of no importance to the present invention. Many methods of deposition, extrusion, coating, cladding and covering are conventionally known and commercially available and any of the se known processes may be chosen to meet the requirements and convenience of the user. Moreover, the quantity of cladding employed need only be that minimal amount which effectively prevents light energy conveyed by the optical fiber 12 from escaping into the ambient environment or to surrounding fibers. It will be recognized and appreciated therefore, that the depth of cladding 26 as appears within FIGS. 1 and 2 respectively is greatly exaggerated and purposely thickened in appearance in order to show the general relationship; and is without scale or precis e ratios between the cladding 26 and the optical fiber 12.

It will also be recognized that the configuration of the cladding 26 as shown by FIGS. 1 and 2 has been shaped as a circular coating to illustrate only one example embodiment. In one preferred embodiment, it is desirable that the cladding 26 take form in regular geometric form such as a round or circular form. Typically, in other preferred embodiments, the shape of the clading 26 will conform to the form and shape of a fiber strand. The configuration shown in FIGS. 1 and 2, however, are merely one preferred embodiment of the cladding 26 as it extends co-axially along the length of the optical fiber 12. For purposes of added clarity also, FIG. 1 reveals the individually clad, optical fiber strand 10 is partial cross-section to demonstrate the relationship between the optical fiber core 12 and the cladding 26 which is coextensive along its length.

The user also has a variety of choices at his discretion regarding the configuration of the "distal" end 16 of the optical fiber 12 as shown by FIGS. 3A and 3B; however, generally both ends of the strand must be the same—i.e., if the "distal" end is cylindrical then the "proximal" end should be also. As seen in FIG. 3A. The "distal" end 16 is substantially cylindrical in shape and desirably presents a surface 20 which is substantially planar and smooth. A possible, but less desirable, alternative is shown by FIG. 3B, in which the distal end 30 nevertheless provides a very different end surface for the optical fiber 12. The surface 32 includes a depression or well 34 which extends into the substance of the optical fiber 12 at a depth typically of several micrometers. Although the well 34 appears substantially circular within FIG. 3B, oval or other rotund configured depressions may also be employed as fits the needs or convenience of the use. Similarly, the void volume of the well 34 from its greatest depth to the proximal surface 32 may also be varied.

It will be recognized and appreciated as well that the range and variety of dimensional and configurational divergence for the strand end is limited only by the user's ability to subsequently dispose and immobilize a nucleic acid probe of known composition/formulation of controlled thickness or density on the intended distal surface of the optical fiber 12. In some embodiments, a greater depth of deposit on the surface of the distal end surface may be highly desirable; nevertheless, for most general assay purposes, both quantitative and qualitative, the intended distal surface illustrated within FIG. 3A as a substantially planar and smooth surface is deemed to be most suitable and desirable.

A typical preformed fiber optic array, its organization and construction and its component parts are illustrated by FIGS. 4–6 respectively. Each discrete, unitary fiber optic array is a preformed composite comprised of a plurality of individually clad, fiber optical strands disposed coaxially along their lengths. The smallest common repeating unit within the preformed array is thus a single optical fiber strand. The manner in which these optical fiber strands are prepared and the manner in which these prepared optical strands are joined collectively into an organized optic array are conventionally known, but is fundamental to a proper understanding and use of the alternative format.

It is recognized also that the unitary array of optical fibers has been used previously as a major component in other inventions and is described in earlier issued patents. Such usage is exemplified by U.S. Pat. Nos. 5,244,636; 5,320,814; 5,244,813; 5,250,264; and 5,298,741; the texts of which are individually expressly incorporated by reference herein.

The unitary fiber optic array 100 appears in exaggerated, highly simplified views without regard to scale within FIG. 4 The preformed array is typically composed of a plurality of individually clad, fiber optical strands which collectively joined coaxially along their respective lengths as a discrete, unitary optic array 104 of fixed and determinable configuration and dimensions. The optic array 104 has a unitary, rod-like collective body 106 and intended distal and proximal collective ends 108, 110 formed of multiple strand end faces. The intended distal collective end 108 provides a substantially planar and smooth optic array surface 114. In alternative embodiments, the end surface may be have an angular, concave, convex, annular, stepped or irregular profile. The topographical surface 116 is the result of fusing the clad of each fiber optical strand 102 collectively with a fiber material 118 such that the fusion is drawn and appears as a discrete, unitary array. In this manner, the exterior surface 116 of the collective array body 106 may be configured and dimensioned as an assembly in an acceptable and useful manner. It will be recognized and appreciated also that generally, a substantially cylindrical configuration and topography is maintained and presented by the unitary imaging fiber optic array 100 merely as one preferred embodiment. Any other regular or irregular configuration and design may be achieved and employed to satisfy the individual user's needs or desires.

For purposes of clarity and ease of understanding FIGS. 5 and 6 present a very limited and greatly reduced number of individually clad, fiber optical strands 102 present within the preformed optical array 104. A total of only 120 individually clad, fiber optical strands are seen to comprise the optical array 104 in greatly magnified and scale-exaggerated views. Moreover, the relationship of the optical array surface 112 (the intended distal end) with respect to the other optical array surface 114 (the intended proximal end) becomes simplified and more-readily appreciated when using this limited number of 120 optical fiber strands. In practice and reality, however, it is estimated that typically there are 2000–3000 optical fiber strands in a conventional unitary array of 200 $\mu$M diameter, with much higher numbers possible as well with larger diameters. Thus the true total number of individually clad, fiber optic strands forming the unitary imaging fiber optic array will typically be in the thousands and vary substantially with the cross-sectional diameter of each optical fiber and the thickness of the cladding material employed when constructing the optical fiber strands themselves.

The construction, coherent organization, and positional alignment within a typical fiber optic unitary array is revealed by FIGS. 4–6. For descriptive purposes only, each of the individually clad, optical fiber strands is presumed to be linearly straight in position and has been arbitrarily assigned an identifying number S1–S120 as shown via FIGS. 5 and 6. The intended distal optic array end surface 112 of FIG. 5 shows that each of the individual optical fiber strands S1–S120 can be identified and distinguished from its adjacently disposed neighbor as well as from any other optical fiber strand within the preformed array 104 by a set of spatial positioning coordinate numbers for the strand end faces. The intended distal optical array surface 112 may be arbitrarily divided into two axial directions as is illustrated by FIG. 5. The exact location of the S1 strand is thus identifiable by the numerical coordinates "XIID" showing the strand end face. Similarly, the exact spatial positioning and strand end face of the S72 fiber is designated as "VIM." In this manner, the individual spatial position and strand end faces for each optical fiber strand S1–S120 is thus completely locatable and identifiable using the coordinate numeral labeling system.

The other optic array end surface 114 (the intended proximal end surface) allows for a similar mode of identification (presuming straight linear alignment of strands) by spatial positioning of each individual optical strand—again as a result of using dual-axis numerical coordinates as seen in FIG. 6. Accordingly, fiber end strand end face S1 is located at numerical position "12d', and fiber S72 is identifiable, locatable, and distinguishable from all other fibers at the optic array surface by its individual numerical coordinates "6m". In this manner, the precise and exact position of each individually clad optical fiber strand and strand end faces on each of the discrete optic array surfaces 112, 114 can be located, identified, and specified via a series of two different numerical coordinates. Accordingly, when imaging or coherent fiber arrays are used, the intended distal and proximal optic array surfaces are thus completely identifiable and distinguishable as per individual fiber optical strand 102 despite its presence in the preformed collective body 106 of the unitary fiber optical array 100.

It will be appreciated also that the overall organization of the individually clad optical fiber strands 102 within the unitary array 100 of FIGS. 4–6 is as aligned, parallel strands which maintain their relative organizational positioning in a coherent, consistently aligned manner over the entire length of the collective body 106. In one preferred embodiment, a coherent unitary array is a highly desirable and easily fabricated organization scheme for the preformed optical fiber array of the present invention. However, the high degree of organizational alignment of a coherent array is not an absolute requirement for each and every embodiment using an unitary optical array. Alternative manufacturing practices allow for a more random disposition of the individually clad, optical fiber strands disposed coaxially along their lengths. A partially random disposition and a completely random alignment of the optical fiber will also result in a unitary collective body of optical fibers and in proximal and distal collective ends which provide two discrete optical array surfaces. It will be recognized therefore that while the individually clad, optical fiber strands may lie adjacent one another at one end, they may deviate and meander through the length of the array such that their position relative to one another may vary substantially in part or in whole—thereby creating semi-coherent or incoherent positional alignments which vary in the randomness of their organizational construction There is no requirement that the positioning of the intended proximal end of one strand be aligned and/or identical with the positioning of the intended distal end within the unitary optic array. The use of non-coherent unitary fiber optic arrays may be useful in some embodiments wherein light is used to synthesize the array. In these embodiments, the use of either a pinhole mask or conventional photolithography mask for introducing light to a portion of a non-coherent array end surface, where adjacent fiber strands are illuminated during photodeposition, can result in the attachment of nucleic acid probes at a number of different fiber strands at diverse locations on the distal end, as the fiber strands which are illuminated at the proximal end diverge and randomize within the length of the fiber optic array.

The entirety of the construction for the unitary optical fiber array (whether uniformly coherent semi-random, or completely randomly organized) provides a means of introducing light energy photons of any determinable wavelength at one optic array surface with the knowledge that the light energy will exit at the other optic array surface. Therefore, by using the preferred completely coherent and rigidly maintained parallel alignment of strands illustrated by FIGS. 5 and 6 (the intended distal and proximal optic array end surfaces respectively) of a unitary fiber optic array, the user may introduce light energy to a portion or all of the optic array end surface 114 and have accurate knowledge and confidence that the light energy would be conveyed by the fiber strands and exit from the other optic array end surface 112. Conversely, were light energy introduced to the optic array end surface 112, the light energy would be conveyed by the optical fibers of the array and will exit from the other optic array end surface 114.

In addition, the topography of the unitary optic array end surfaces 112 and 114 will vary with the nature of the end faces for the individual optical fibers strands comprising the array. Thus, if the optical fiber strand end faces conform to that illustrated by FIG. 3A then the array end surface will present a substantially planar and smooth topography. Alternatively, however, if the optical fiber end faces forming the array are exemplified by FIG. 3B; then the unitary array end surface will appear as a collective of wells or depressions, each well extending into the collective substance of the array end surface at a set depth (typically of a few micrometers). The topography of the unitary array end would then present a pitted and crater-like surface for the immobilization of oligonucleotides as fixed probes.

It will also be recognized that the user may chose to introduce light energy to only a specific spatial location on the optic array end surface 114—for example, only to fibers S1. S7 and S8—and have accurate knowledge and confidence that the light energy would be conveyed only by those three optical fiber strands and exit from numerical positions "XIID", "XIC", and "XID" alone on the optic array end surface 112. Generally, no other light energy would appear from any other spatial position from the optic array surface 112. Similarly, were light energy of specific wavelength introduced at the optic array surface 112 via fibers S107, S108, and S115, respectively, the use can accurately predict and identify that the light energy will be conveyed by only these three optical fibers; and will exit only at the optic array surface 114 of numerical coordinate position numbers 2c, 2d, and 1d respectively and from no other spatial positions on this optic array surface. In this manner, not only does one have knowledge of the individual spatial positioning of each optical fiber strand in the preformed array but also one has the ability to identify and precisely locate light energy photons emerging from individual optical fiber strands within the whole of the optic array surface in a practical and reliable mode.

Accordingly, a unique feature and key requirement of the unitary optical fiber array construction allows and demands the capability for precise spatial positional introduction and conveyance of light energy via different fiber optical strands within the collective body of the preformed, unitary fiber optical array. This capability to introduce light energy at precise spatial positions at one end surface of a unitary array, to convey the introduced light energy along the length of a selected individual fiber optical strands, and to control the exit of the conveyed light energy at an opposite end surface at precisely known spatial positions on the opposing end surface is a unique feature and distinct advantage of the of the unitary fiber optic array sensor disclosed herein, sensor presented herein.

The fiber optic array further comprises nucleic acid probes attached to the individual fiber strands. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to increase the stability and half-life of such molecules in physiological environments.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occuring nucleic acids and analogs may be made.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as a nucleoside.

The nucleic acid probes of the present invention are designed to be complementary to a target sequence (either the target sequence of the sample or to other probe sequences, for example if sandwich hybridization assays are used, as is known in the art), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

As is appreciated by those in the art, the length of the probe will vary with the length of the target sequence and the hybridization and wash conditions. Generally, oligonucleotide probes range from about 8 to about 50 nucleotides, with from about 10 to about 30 being preferred and from about 12 to about 25 being especially preferred. In some cases, very long probes may be used, e.g. 50 to 200–300 nucleotides in length.

Each specie of DNA (or RNA, or PNA) fragments is disposed as an individual deposit on at least one strand end face or as multiple independent deposits in aligned organization on multiple strand end faces at one or at many different spatial positions on the distal optic end surface. Each oligonucleotide specie deposit on an optical fiber strand end face, therefore, serves as one fixed probe immobilized at a predetermined spatial position; and in each of the array formats, the multiple fixed probes serve collectively as many singular and different reaction zones acting repetitiously and in common for in-situ hybridization with a mobile complementary nucleic acid target (directly or indirectly bearing a joined identifying label).

Preferably, the oligonucleotide probe should bind with its intended target at each and every instance and occasion where the complementary target species is presented for reactive contact. Thus, although the complementary target sequence may exist in single or low copy number and/or be encased in a larger-sized fragment containing non-complementary sequences, the oligonucleotide probe should nevertheless bind to the target portion of these larger mobile fragments when they come into reactive contact with the probe. Such binding capacity provides both specificity and sensitivity for the biosensor as a whole.

The nucleic acid probes used on the array are preferably covalently attached to the distal end faces of the array. That is, in a preferred embodiment, one species of probe is attached to at least a first strand end face, a different species of probe is attached to at least a second strand end face, etc. In some embodiments, each probe may be attached to more than one end face, which may or may not be contiguous with adjoining end faces; that is, a single probe species may be attached to a "spot" comprising a plurality of end faces, or a single probe species may be attached to a number of discretely placed and separated end faces, depending on the way the array is made and the required sensitivity. That is, it may be desirable to have the signal reflect the addition of signal from different fibers in some embodiments.

When depositing the individual DNA or RNA oligonucleotide specie to be used as a probe on the end surface of a single optical fiber strand or at precisely spatially positioned locations on one optical array end surface, it is necessary that the oligonucleotide(s) remain immobilized at the single or the different spatial positions assigned to each of them individually without migrating towards any other position. Multiple methods of oligonucleotide probe deposition and immobilization are conventionally known and are suitable for use in making an embodiment of the present invention. Thus, one may prepare a specific formulation comprising one specie of nucleic acid bases in sequence and dispose the formulation at a specific spatial position and location on the optic end surface.

As will be appreciated by those in the art, there are a wide variety of attachment techniques for the attachment of nucleic acid species to a solid support such as a fiber optic array.

As will be appreciated by those in the art, the method of making the oligonucleotide arrays of the present invention may vary. In a preferred embodiment, oligonucleotides are synthesized using traditional and well-known methods and then attached to the support surface. Alternatively, the oligonucleotides may be synthesized on the surface, as is known in the art. Preferred methods are outlined herein and are known in the art; see WO 95/25116; WO 95/35505; U.S. Pat. Nos. 5,700,637 and 5,445,934; and references cited within, all of which are expressly incorporated by reference.

Among the conventional practices of deposition a variety of generally applicable polymerization processes are known, including thermal techniques, ionization methods, plasma methods, and electroinitiation procedures. These different methodologies are exemplified by the following publications, the text of each being expressly incorporated by reference herein. Thermal methods: Graham et al., J. Oral Chem. 44: 907 (1979); Stickler and Meyerhoff, Makromal. Chem. 179:2729 (1978): and Brand et. al, Makromol. Chem. 181: 913 (1980). ionization methods: A. Chapiro, Radiation Chemistry of Polymer Systems Chapter IV. Wiley-Intersciences. Inc., New York. 1962: J. E. Wilson, Radiation Chemistry of Monomers, Polymers, and Plastics, chapters 1–5, Marcel Dekker, New York. 1974. Plasma methods: Yasuda. W. and T. S. Hsu, J. Polym. Sci. Polym. Chem. Ed. 15: 81 (1977): Tibbett et al., Macromolecules 10: 674 (1977) Electroinitiation method: Pistoria. G. and O. Bagnarelli, J. Polym. Sci. Polym Chem. Ed. 17:1001 (1979): and Philips et al., J. Polym. Sci. Polym. Chem. Ed. 15:1563 (1977)

In general, the end face of the array and the nucleic acids may be chemically functionalized to contain chemical functional groups that can be used for attaching the nucleic acids. Preferred functional groups for attachment are amino groups, carboxy groups, oxo groups and thiol groups, with amino groups being particularly preferred. Using these functional groups, the nucleic acids are attached to the end face of the array. In some embodiments, linkers can be used as well, as is known in the art; for example, homo-or heterobifunctional linkers as are well known (see 1994 Pierce Chemical Company catalog, technical section on crosslinkers, pages 155–200, incorporated herein by reference).

In a preferred embodiment, the deposition and immobilization of the nucleic acids utilizes photoactivation/photodeposition techniques. For example, a preferred embodiment utilizes the composition of the surface and the method of attachment is as described in U.S. Pat. Nos. 5,427,779; 4,973,493; 4,979,959; 5,002,582; 5,217,492; 5,258,041 and 5,263,992, and references cited therein, all of which are hereby expressly incorporated by reference. Briefly, coupling can proceed in one of two ways: a) the oligonucleotide is derivatized with a photoreactive group, followed by attachment to the surface; or b) the surface is first treated with a photoreactive group, followed by application of the oligonucleotide. Preferably, the activating agent is N-oxy-succinimide, which is put on the surface first, followed by attachment of a N-terminal amino-modified oligonucleotide, as is generally described in Amos et al., Surface Modification of Polymers by Photochemical Immobilization, The 17th Annual Meeting of the Society of Biomaterials, May 1991, Scottsdale AZ, hereby expressly incorporated by reference. Thus, for example, a suitable protocol involves the use of binding buffer containing 50 mM NaPhosphate pH 8.3, 15% Na2SO4 and 1 mm EDTA, with the addition of 0.1–10 pMole/$\mu$l of amino-terminally modified oligonucleotide. The sample is incubated for some time, from 1 second to about 45 minutes at 37° C., followed by washing (generally using 0.4 N NaOH/0.25% Tween-20), followed by blocking of remaining active sites with 1 mg/ml of BSA in PBS, followed by washing in PBS.

These particular methods allow the use of a large excess of an oligonucleotide, preferably under saturating conditions; thus, the density and uniformity of the application is high.

In addition, photoactivaction techniques utilizing photopolymerization compounds and techniques are used. One embodiment employs one or more photoactivated monomer preparations in admixture with one species of oligonucleotide as a photopolymerizable formulation [the latter described in Munkholm et al., Anal. Chem. 58:1427 (1986) and Jordan et al., Anal. Chem. 59: 437 (1987)]. Such monomer preparations typically comprise solutions of several monomers in admixture and a concentration of the chosen DNA or RNA oligonucleotide specie. A representative listing of different monomer compositions suitable for preparing an admixture which subsequently can be photopolymerized are given by Table 1 below.

It will be appreciated that the listing of Table 1 are merely representative of the many different substances which can be usefully employed in admixture with a specie of oligonucleotide or as photoactivatable coatings for the end face for subsequent attachment of the nucleic acid. In addition, the scientific and industrial literature provides many alternative monomer preparations and admixtures which are also suitable for use in making the present invention. Accordingly, all of these conventionally known monomer preparations are considered to be within the scope of the present invention.

TABLE 1

A. Monomers
acrylamide
N,N-methylene bis (acrylamide)
hydroxyethylmethacrylate
EGDMA
vinyl acetate
(N-(3-aminopropyl) meth-acrylamide hydrochloride [Kodak, Inc]
N-acryloxy succinimide In a preferred embodiment, the nucleic acids can be synthesized in situ, using well known photolithographic techniques, such as those described in U.S. Pat. No. 5,445,934 and related applications and publications; these methods of attachment form the basis of the Affimetrix GeneChip™ technology.

In a preferred embodiment, the oligonucleotides are covalently attached to the support surface, using the techniques described herein. In an additional embodiment, the attachment may be very strong, yet non-covalent. For example, biotinylated oligonucleotides can be made, which bind to surfaces covalently coated with streptavidin, resulting in attachment.

A preferred method of making the present arrays involves a serial photodeposition technique, using the methods outlined above. Generally, the distal end face is completely functionalized with a photoactivatable compound. The nucleic acid is contacted with at least one strand end face, either by coating the entire array end face with a nucleic acid solution or by the application of a drop or spot of nucleic acid reagent. Light is introduced, at either the proximal or distal end, to sequential individual fibers or groups of fibers to activate the photoactivatable compound and attach the nucleic acid. This process can be repeated for the attachment of each nucleic acid probe species. In some embodiments, a mask, such as a photolithographic mask may be used, at either the proximal or distal end, to precisely control the location and/or size of the activated area.

In addition, the compositions of the invention generally further comprise light sources and light detectors, as is more fully outlined below. Once made, the compositions of the invention find use in a number of applications. In a preferred embodiment, the compositions of the invention are used to detect target sequences in a sample. The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined herein, probes are made to hybridize to target sequences to determine the presence or absence of the target sequence in a sample. Generally speaking, this term will be understood by those skilled in the art.

If required, the target sequence is prepared using known techniques. For example, the sample may be treated to lyse the cells, using known lysis buffers, electroporation, etc., with purification and/or amplification such as PCR occuring as needed, as will be appreciated by those in the art.

The analyte of interest to be detected optically using the biosensor and supporting apparatus is at least one mobile complementary oligonucleotide target specie bearing an identifying label joined directly or indirectly. The complementary target specie represents a sequence of nucleotides which corresponds as the complementary base sequence to the nucleic acids comprising the fixed oligonucleotide probe. It is expected and envisioned that the mobile complementary target specie will bind selectively to and hybridize in-situ with the nucleic acid sequence of the probe; and thereby generate a reaction product which is the result of specific and selective binding between only the fixed probe specie and the complementary target specie.

The present invention also intends and expects that an in-situ hybridization reaction will occur between each probe immobilized at one position or at multiple and differing spatial positions as fixed probes, and the target sequence, to form a specific hybridization complex. Preferably, cross-hybridization reactions are minimized, although this may be useful in mismatch identification, as is known in the art. In this manner, different kinds of individually labeled target species will react with only their counterpart and corresponding fixed probes on at least one and preferably at several individual and differing spatial positions on the distal array end surface. Thus, at the users choice and option, the array formats of the biosensor may be utilized to selectively detect only one mobile target species or a plurality of different target species intermixed in a fluid sample.

Generally, there are three requirements for each target sequence to be detected using the present invention. These are: that the target sequence be mobile; that the target sequence ultimately bear a directly or indirectly joined identifying label; and that the target sequence be present in a fluid sample placed into reactive contact with the distal end of the biosensor. It will be noted and appreciated also that while there is no requirement as such, it is often desirable that the individual complementary oligonucleotide target specie be separated, isolated, purified or semi-purified before being placed into reactive contact in order for an effective in-situ hybridization to occur. Thus, the fluid sample often may comprise a mixture of different materials including not only multiple nucleic acid sequenced fragments, some of which are the complementary target specie for hybridization; but also may contain some extraneous matter, such as cellular debris or unrelated pharmacologically active molecules which typically are present only as incidental remnants from an earlier extraction, reaction, or preparation process. As a general rule, therefore, the fewer the number of extraneous chemical entities in the fluid sample, the faster the kinetics of in-situ hybridization will proceed and the cleaner the results.

In a preferred embodiment, the target sequence bears at least one label, preferably a light energy absorbing dye is bound initially or becomes linked subsequently to each target sequence as an identifying label. If desired, more than one dye reagent can be employed as a joined identifying label.

Each light energy absorbing dye formulation or composition will be bound directly or becomes linked indirectly to the one specie or to multiple different species of oligonucleotides intended for use as complementary targets. Moreover, each dye will then show evidence of its presence by either absorbing and reflecting a portion of the light energy: or, alternatively, by absorbing light energy and then subsequently emitting light energy of a different wavelength in return. Such reflected or emitted light energy is can be detected at either the proximal or distal end, although preferably it is intended to be conveyed from the distal end surface: and such conveyed light will emerge from the proximal end surface for detection and measurement.

The various dyes which may be bound initially or linked subsequently to a chosen oligonucleotide fragment as a joined identifying label are all conventionally known intends that ail the commonly useful properties and capabilities of the various classes of light energy absorbing dyes be employed directly and indirectly, and as needed or desired for the specific use or application. Merely illustrative of the many different dyes are those fluorophores, indirect (secondary) labels, and interchelators listed below within Tables 2, 3, and 4 respectively.

TABLE 2

| Compounds | Excitation Wavelength (range or maximum) | Fluorescence emission range (max) |
|---|---|---|
| A. Fluorophores | | |
| Eosin | 520–530 nm | 530–580 nm (550 nm) |
| TRITC-amine | 555 nm | 570–619 nm (590 nm) |
| Quinine | 320–352 nm | 381–450 nm |
| Fluorescein W | 488–496 nm | 530 nm |
| Acridine yellow | 464 nm | 500 nm |
| Lissamine Rhodamine B Sulfonyl Chloride | 567 nm | 580 nm |
| Erythroscein | 504 nm | 560 nm |
| Ruthenium (tris, bipyridium) | 460 nm | 580 nm |
| Texas Red Sulfonyl Chloride | 591 nm | 612 nm |
| B-phycoerythin | 545, 565 nm | 575 nm |
| Nicotinamide adenine dinucleotide (NADH) | 340 nm | 435 nm |
| Flavin adenine dinucleotide (FAD) | 450 nm | 530 nm |
| Carboxy Seminaphthorhydafluor | 587 nm | 640 nm |
| Naphthofluorescein | 594 nm | 663 nm |
| Carboxy Fluorescein (Fam) | 495 nm | 520 nm |
| BODIPY* | | |
| JOE* | | |
| TAMRA* | 540 nm | 564 nm |
| ROX* | 567 nm | 591 nm |
| B. Fluorescent Antibody Conjugates | | |
| Protein A fluorescein conjugates | 480 nm | 520 nm |
| Anti-Atrazine fluorescein Conjugates | 480 nm | 520 nm |
| digoxin-Anti-digoxin Texas Red Conjugates | 590 nm | 615 nm |

*Trademarks of Molecular Probes Inc. (Eugene, OR)

It will be recognized and appreciated also that the available range variety, and diversity of light energy absorbing dyes, dye formulations, and dye mixtures is not dependent upon a single light source or light energy supply in order to be effective. Although light energy of determinable wavelengths is desirably provided by electrical light sources—that is, light emitting diodes (LEDs), lasers, laser diodes and filament lamps whose bands of light energy are typically controlled and selected by filters, diffraction gratings, polarized filters or alternatively broken into various broad wavelengths of light energy via prisms, lenses, or other optical/spectral articles—these are not exclusively the only source of useful light energy. Clearly, in various applications and circumstances other less typical light energy sources will also be useful. Accordingly, neither the true source, nor the nature of light energy photons nor the manner in which they are conveyed or otherwise caused to be created is of importance or consequence.

In addition, the dye label individually may comprise a pair of specifically binding materials such as the chemical compounds listed within Table 3 for subsequent reactive contact and indirect juncture of an identifying label. Thus each dye label individually may in fact be formulated as a composite comprising light emitting dye in part; and include a variety of receiving elements which are able to interact as specific binding partners for joining the light energy dye label subsequently. Exemplifying some multiple formulations and combinations are those described below and used experimentally hereinafter.

TABLE 3

Secondary Label Pairs
(Labels include but are not limited to those mentioned in Table 2)

| | |
|---|---|
| Biotin | Labeled avidin/streptavidin |
| Protein A | Labeled IgG |
| Digoxin | Labeled anti-digoxin |
| Enzymes such as: | |
| alkaline phosphatase | diphosphate derivatives |
| | ELF-97 substrates (enzyme activated) |
| β-glucuronidase | glucuronide |
| | galactopyranoside |
| Horseradish Peroxidase | |

A range of different preparation methods and processes are conventionally known and available in the published scientific literature for creating a target sequence of known base sequence joined directly to an identifying label as a conjugate. Representative of and exemplifying these direct attachment procedures are the following: Agrawal et. al., Nucleic Acids Res. 14: 6227–6245 (1986); Smith et. al., Nucleic Acids Res. 13: 2399–2412 (1985): Cardullo et. al., Proc. Natl. Acad. Sci. USA 85: 8750–8794 (1988). J. Fluorescence 1: 135 (1991).

An alternative preparation strategy and procedure is exemplified by incorporation of biotin, in the form of a biotinylated nucleotide (such as biotin-d UTP) into the nucleic acid structure using conventional procedures such as nick translation or tailins [Rigby et. al., J. Mol. Biol. 113: 237 (1977); Lobban. P. E and A. D. Kiser, J. Mol. Biol. 78: 453 (1973)]. The selective binding of the biotinylated targeted to the fixed probes in the in-situ hybridization reaction may then proceed in the absence of the dye label itself. Subsequently a conjugate complex constituted of avidin or streptavidin (proteins with a high affinity for binding to biotin) covalently are linked to a fluorescent or color reflecting dye ligand is then added as a dye label complex to the reaction fluid after hybridization has occurred; and the selective binding capability for the paired agents will then cause the identifying dye label to be joined via the avidin (or streptavidin) indirectly to each biotinylated target species wherever it is found. Qualitative and quantitative optical detection of the hybridized target specie can therefore be made on the basis of the spectral characteristics of the ultimately and indirectly joined identifying label. The listing of Table 3 provides other alternative pairs of specific binding agents suitable for use.

If desired, a biotinylated complementary target specie may be also prepared using polymerase chain reaction processing. The biotinylated amplified product obtained by PCR methodology may be used immediately or purified before being placed into reactive contact with the biosensor. Also, any of the other pairs listed in Table 3 may be substituted for use in the PCR method.

In addition, the user may optionally employ the technology known as enzyme-labeled fluorescence (ELF) signal amplification to provide a joined identifying label. This technology is described in detail by U.S. Pat. Nos. 5,136,906 and 5,443,986, the texts of which are expressly incorporated by reference herein. In brief an enzyme such as alkaline phosphatase is attached directly or is linked subsequently to the complementary oligonucleotide target species. The substrate for the enzyme's catalytic activity is one which provides an intense fluorescent signal and also demonstrates a very large Stoke's shift. Such substrates have been shown to be highly detectable labels when used with conventional in-situ hybridization method. See for example: Am. J. Human Genet. SUPPI. 55. A271, Abstract X1588 (1994); FASEB J. 8: A1444, AbstractX1081 (1994); and Mol. Biol. of the Cell SUPDI 4, 226a, Abstract #1313 (1993).

The user is thus given the option of preparing the complementary oligonucleotide target specie in several ways. The target specie nucleic acid sequence may be directly and immediately bound to an identifying dye label(such as those of Table 2) if desired. Alternatively, the complementary oligonucleotide target specie or species may be prepared as molecules having a receiving element such as biotin. The biotinylated target specie is allowed to hybridize in-situ with the fixed probes on the distal end surface of the biosensor; and then a prepared specific binding partner (such as avidin or streptavidin complex) bearing an identifying dye label as a component part can then be added to the reaction fluid after hybridization is completed—thereby causing the identifying label to be joined subsequently as well as indirectly to the immobilized hybridized reaction product. Finally, the intercelators (such as those listed within Table 4), may be used in unmodified form to label double-stranded, hybridized reaction products without any prior intermediate agent. The target species thus remains unlabeled throughout the entire hybridization process: the intercelators then will bind directly to the double-stranded reaction product upon reactive contact.

TABLE 4

Intercalators ethidium bromide;
Cy-5;
Ru (byp)$_2$ MCCP;
Hoechst 33258 (bis-benzimide);
Cyanine dyes*

TOTO ®
YOYO ®
BOBO ™
POPO ™
SYBRI ®

*Trademarks of Molecular Probes Inc. (Eugene, OR)

The labeled target sequence is contacted with the distal end face of the array, under conditions which facilitate the formation of a hybridization assay complex between the probe and the target sequence.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. The hybridization conditions may also vary when a non-ionic backbone, i.e. PNA is used, as is known in the art. In addition, cross-linking agents may be added after target binding to cross-link, i.e. covalently attach, the two strands of the hybridization complex.

The optical biosensor of the present invention intends and requires that a species-specific, in-situ hybridized reaction product or complex result as the consequence of a selective reactive contact between a mobile target sequence with a label and one or more oligonucleotide probes deployed either on the distal end surface of an unitary fiber optic array that relies upon spatial resolution as a means by which to differentiate and distinguish among the alternatively positioned hybridized complementary target species concurrently immobilized at many differing spatial locations on the optic array surface. It is the combination of fixed spatial positionings for in-situ hybridization at the differing chosen locations and the spatial resolution capability to separate and distinguish the joined identifying dye label among the different fixed surface positionings (and the different, hybridization reactions occurring concurrently) which avoids and eliminates random intermixing of individual light energy photons traveling to and from an identifying label concomitantly joined to each in-situ hybridized reaction product formed on the optic array surface of the biosensor.

Thus, within the in-situ hybridization zone on the distal end surface, each label joined to a target sequence that is immobilized becomes, in turn, concomitantly immobilized and disposed only at individual probe locations fixed on the optic array end surface; and the presence of a joined identifying label held at any one or more fixed spatial positions can only be the secondary consequence of a specie-specific in-situ hybridization reaction having occurred at that spatial position. Each immobilized identifying dye label will then show evidence of its presence at that precise spatial position by either absorbing and reflecting a portion of the light energy or absorbing light and then subsequently emitting light energy of a different wavelength in return. Such reflected or emitted light energy is conveyed via one or more individual fiber optic strands in aligned position with the immobilized dye itself. Such conveyed light will emerge from the other optic end surface only at precisely located spatial positions; and thus be distinguishable as such from other light energy conveyed by any other fiber optical strands via the precise spatial positioning and the spatial resolution of the emerging light at the optic array surface. In this manner, the conventional limitations and demands of single channel optical fibers are eliminated since the strands within the fiber optical array retain the spatial positioning for each of the disposed dye labels. Thus, the traditional requirement for spectral resolution is removed due to the ability by the fiber optical array to resolve each of the dye labels spatially.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1
A Preferred Method Of Making A Biosensor

To demonstrate a most desirable method of making the biosensor comprising the present invention: and as a demonstration of the effectiveness for making optical determinations using the fully constructed fiber optic sensor, a detailed description of the manipulative steps for making a sensor able to: hybridize in-situ with and consequently detect a mobile complementary oligonucleotide target specie bearing an identifying dye label is presented. It will be expressly understood, however, that the detailed description which follows hereinafter is merely illustrative and representative of the many different kinds of biosensors utilizing a unitary fiber optic array which can be made having one or more individual species of oligonucleotides deposited as multiple fixed probes at precise spatial positions on the optical array end surface, each disposed species-selective fixed probe being able to react with and individually hybridize with a labeled mobile complementary target specie of oligonucleotide which is of interest in a fluid sample.

Surface Silanization

Initially, fiber optic array similar to that illustrated by FIGS. 4–6 respectively was obtained from commercial sources [Applied Fiber Optics, Inc., Southbridge, Mass.]. One optical array surface was submerged in a acetone 10% solution of 3-(trimethoxysilyl) propyl-methacrylate dispersed in dry acetone and allowed to soak for 2 hours duration. After silanization, this optical array surface was rinsed first with dry acetone and then with distilled water.

Light Source

A fiber optic connector and ferrule [AMP, Inc., Harrisburg, Pa.] were modified to physically secure the fiber optic array to a fiber optic lighting cable for transporting light energy of varying wavelengths to precise spatial positions on the distal array surface of the imaging fiber optic array. The exterior surface of one representative fiber optic lighting cable is illustrated in an enlarged view by FIG. 7.

An inspection of the lighting cable of FIG. 7 reveals (in an exaggerated, highly oversimplified view for purposes of clarity) that the individual light sources via coordinated numerals correspond precisely to the spatial positions of FIGS. 5 and 6 and are directly aligned with individual fiber optical strands S1–S120 (which also are precisely positioned spatially and identifiable via linear coordinates). Thus, light originating from source L1 will be introduced only to fiber S1 spatially positioned at coordinate number "12a": similarly, light energy emanating from source L85 will be introduced only to that precise spatial position on the proximal optical array end surface identifiable as fiber S85 at coordinates "4a". In this manner, only predetermined and prechosen fiber optical strands will receive light energy of determinable wavelengths for a specified duration, at a time desired by the user alone, and no other optical fiber strand will receive any light energy whatsoever other than those strands located at a precise spatial position on the surface of the optic array surface. By purposeful choosing, therefore, of which fibers on the fiber optic lighting cable are to be illuminated, the user may introduce light energy at will to only pre-chosen, precise spatial positions and only to those few fiber optical strands known to be present at precisely that location alone on the optical array surface. By employing such a lighting cable for illuminating individual fiber strands of the unitary fiber optic array during photodeposition of oligonucleotides, individual oligonucleotide species may be precisely deposited on either portions of a distal end surface covering multiple end surfaces of individual fiber strands, at predetermined locations and regions of a distal end surface, or on individual fiber strand end faces on a distal end surface of a unitary fiber optic array. In alternative embodiments, a mask may be employed with a fiber optic lighting cable to produce a pattern of oligonucleotide deposits on a distal end surface of the unitary fiber optic array, where discrete deposits may be formed on individual fiber strand end faces or across a group of adjacent fiber strand end faces. In some embodiments, the fiber optic lighting cable of FIG. 7 need not be employed where precise location of oligonucleotide deposits is not required. In these embodiments, the oligonucleotide deposit will typically encompass a surface area greater than the diameter of a single fiber strand and it is unnecessary to employ a fiber optic lighting cable of such precise one-to-one correspondence as that shown by FIG. 7.

Typically, where precise location of photodeposited oligonucleotides is not require, a lighting apparatus having either a pinhole or a conventional mask in a holding device which allows fine focusing and precise placement of light is employed in the making of the sensor. In this embodiment, where either a pinhole or mask is employed, only one light source utilized rather than a fiber optic lighting cable having multiple light sources; and the light passing through either the pinhole or mask acts as a light source to introduce focused light energy to a portion of the unitary array end surface. Typically, when a pinhole or masked light source is employed, multiple fiber strands are illuminated simultaneously. Where a pinhole light source is employed, the illuminated strands may be adjacent positioned, neighboring fiber strands. For example, a single pinhole light source permits the deposition of an oligonucleotide, or oligonucleotide- monomer admixture, over multiple strand faces simultaneously. When a pinhole light source is employed with a coherent unitary fiber array, or imaging fiber, the resultant deposit is formed on a group of adjacent fiber strands, either as a single discrete deposit across multiple fiber ends or a plurality of discrete deposits on individual fiber ends, at the distal end of the unitary fiber optic array.

When a pinhole light source is employed with an incoherent, or random, unitary fiber array, the resultant deposit is formed on the ends of individual fiber strands which are randomly disperesed across the distal end of the unitary fiber optic array. The advantages and benefits of using a pinhole source of focused lighting are that a controlled volume of admixture is precisely deposited at the pre-chosen spatial position on the optic array surface with minimal time and labor. Alternatively, when a masked light source is employed, the illuminated strands conform to the mask image which may extend, as a prechosed pattern, over multiple fiber strand end faces across a diverse region of the unitary array end surface.

The fiber optic lighting cable of FIG. 7, although having unique capabilities for precisely illuminating individual fiber strands, is typically unnecessary for many practical applications and is provided only as as an example for demonstrating the principle of introducing light energy to a precise location on the proximal optic array surface and is used merely to illustrate the method and the manner in which the oligonucleotide may be attached by photopolymerizatoin at precisely positioned, pre-chosen locations on the distal unitary fiber optic array end surface. Having illustrated both the principle and the intended results, it will be recognized and appreciated that any lighting source of any correspondence with the fiber optical strands of the fiber optic array will serve so long as the disposed oligonucleotide specie deposits are spatially separate and spatially distinguishable from one another on the optic array surface.

Photopolymerization

The manipulations performed during photopolymerization are illustrated via FIGS. 8–13 respectively. For descriptive purposes only, the general magnified and oversimplified construction of the unitary fiber optic array surface of FIG. 5 and the fiber optic lighting cable of FIG. 7 will again be used. As seen within FIGS. 8–13 a fiber optical connector 130 and illumination source 140 provide the capability for illuminating specific areas of one optic array surface of the imaging fiber optic array described previously. Thus, the light energy photons emanating from the surface of the illumination source 140 of FIG. 8 are produced by only light sources L23 L24 and L34 respectively. Only light energy at those precise spatial positions is directed towards the proximal optic array surface 114 of the unitary fiber optical array 100. Consequently as shown via FIG. 8 only those fiber optical strands located at spatial position coordinates 10k, 10l, and 9k respectively receive the light energy photons provided by the illumination source 140. Then as illustrated by FIG. 9, only those corresponding individually clad fiber optical strands S23, S24 and S34 convey the introduced light energy through the body of the unitary fiber optical array 100; and the light exits at the distal optic array end surface 112 only at precise spatial positions (that is, solely at coordinate numbers XK, XL, and IXK as seen within FIG. 5 above. It will be recognized and appreciated that no other spatial positions on the distal array end surface 112 are illuminated during this manipulation.

As the light energy photons emerge from the distal array end surface 112 at only the precise spatial positions indicated by FIG. 9, the optic array end surface 112 lies submerged in a prepared first monomer admixture. The light employed at only this precise spatial positions was prechosen to be at a set wavelength for photopolymerization and the optic array end surface was allowed to react with the first monomer preparation for approximately 30 seconds duration. The reactive contact between the first preparation and the light energy initiated a photopolymerization reaction on the distal array end surface and caused a deposition and an immobilization of the first deposit only at those illuminated spatial positions. Thus, at the end of the allotted reaction time for photopolymerization, a discrete deposit volume 150 was deposited and immobilized solely on the distal optic array surface solely at spatial positions XK, XIK, and IXK. No other fiber strands were illuminated: no other fiber strands conveyed any light energy whatsoever: and no photopolymerization or deposition occurred at any other spatial positions. This is illustrated by FIG. 11.

After the first polymerization was completed, the illumination source 140 was then used again to illuminate the light positions corresponding to light position L15, L16, an L27. Light energy from only these positions introduced light energy photons precisely to the proximal optic array end surface 114 only at coordinate positions 10b, 10c, and 9c. This caused the introduced light energy photons to be conveyed solely by fibers S15, S16 and S27. No other fiber strands were illuminated and no other fiber strands conveyed any light energy whatsoever. This is illustrated by FIGS. 11 and 12. Consequently, as appears in FIG. 12, light energy photons carried by only these individually clad, fiber optical strands (S15, S16, and S27) cause the light to be conveyed and to exit from the distal optic array end surface 112 only at coordinate position numbers XB, XC, and IXC. The optic array surface was then immersed in a second prepared mixture and the light energy allowed to react with this prepared mixture for a predetermined duration. During this reaction time, photopolymerization proceeded and the second deposit was deposited solely at those spatial positions which were illuminated. In this manner, multiple deposits at different locations became immobilized by photopolymerization at only those precisely illuminated locations identifiable by the coordinate numbers XB, XC and IXC. At the end of the allotted time for reactive contact, the distal optic array end surface of the imaging fiber optic array was removed from the second preparation and revealed the deposition of an immobilized deposit of a second preparation material at the precise spatial positions identifiable precisely by coordinate numbers XB, XC and IXC. A discrete photodeposited cone-shaped deposit 160 of the second prepared material species is seen extending from the distal optic array end surface as illustrated by FIG. 15.

Where it is desirable to form discrete deposits on individual, single fiber strand end faces, several fabrication methods are available. In one embodiment, discussed in the preceding sections, a fiber optic lighting cable may be employed for illuminating individual fiber strands of the unitary array during photodeposition. In another embodiment, by choosing specific reactants, catalysts, concentrations, temperature, light flux and exposure times, discrete deposits may be formed on the end faces of individual fiber strands in the unitary array by control of the photodeposition reaction conditions. In an alternative embodiment, where an incoherent, or random unitary fiber array is employed, illumination of a portion of the proximal surface of the incoherent unitary array with a pinhole light source will produce randomly dispersed discrete deposits on the end faces of individual fiber strands across the distal end surface of the array. With any of these embodiments, an optical mask may be employed with a light source to produce a replicated deposit image of the mask, formed as discrete deposits on individual fiber strand end over a portion of the distal end face of the unitary array. With respect to methods for photodeposition of discrete deposits on individual fiber strands, U.S. Ser. No. 08/519,062, filed Aug. 24, 1995 is a particularly useful reference and is expressly incorporated by reference herein.

The practitioner ordinarily skilled in this field will by now also recognize that there is no requirement or demand that an illumination fiber or fiber optic lighting cable as such be employed in this photoactivated method for making the sensor. To the contrary, one merely needs to introduce either pinpoints of light or illuminated mask images onto portions the unitary fiber optic array end surface for photopolymerization to proceed. Thus, for example, one could achieve equivalent effects using lenses, masks, filters, and other light sources. Accordingly, any conventionally known means or manner of introducing light to the unitary array is deemed to be within the scope of the present invention.

The results of the completed photopolymerization process are illustrated by FIG. 13 in which the polymerized first oligonucleotide specie deposit 150 and the polymerized second oligonucleotide specie deposit 160 are individually located and identifiable at precise spatial positions on the distal optic array end surface. It will also be recognized that much of the distal optic array surface 112 remains unencumbered and unobscured: and that were additional light introduced at the proximal array end surface 114 at any of the unobscured strand spatial positions such light photons would be conveyed and would exit from the distal optic array end surface 112 as unencumbered light energy which does not affect or influence the discrete deposits 150, 160 positioned separately nearby.

The Optical Sensing Apparatus And Instrumentation System

In order to be effectively employed, the prepared biosensor is combined with optical apparatus and instrumentation and is utilized as a system to detect and identify one or more specific olignucleotide analytes or nucleic acids of interest. A generalized and representative optical apparatus and instrumentation system which comprises conventional optical components which are commercially available is illustrated by FIG. 14. Sensor measurements may be performed using the apparatus shown schematically by FIG. 14 in the following manner: White light from an excitation source 200 (such as an arc lamp) is collimated; focused by a lens 201; is passed through an excitation filter 202; and is focused on an optic sensor 205 via a 1OX microscope objective 204. The optic sensor 205 is held in an xyz-micropositioner 206 which allows for fine focusing. Excitation light is transmitted and illuminates each thin film sensing receptor unit in the array of the sensor which individually fluoresces in proportion to analyte concentration. The returning fluorescence light is reflected 90° by the dichroic filter 203; desirably, but optimally passed through a beam splitter cube 208; filtered at an appropriate emission wavelength by emission filter wheel 210: and then is detected by the CCD camera 220. Ratiometric measurements are obtained by monitoring fluorescence while switching between two excitation filters 202 using the emission filer wheel 210. The CCD camera typically contains a photosensitive element and may be coupled to an electronic intensifier: which in turn is connected to a computer having a Video Frame Grabber graphic card that digitalizes and processes the video image. Visual imaging is achieved by using a CCD video camera to collect the light which is reflected 90° by the beam splitter cube. Illumination for visual imaging purposes is achieved either by rotating the excitation filter wheel to an empty position (using neutral density filters as necessary); or by illuminating the sample and its environs at the distal end of the sensor with an independent light source.

The optic sensing apparatus and instrumentation system shown by FIG. 14 detects fluorescence either as light intensity or as light wavelengths—that is, a spectral response generated by and released by a deposited probe from a single optical fiber strand end surface; or from at least one strand end face in a bundled array of single core fibers; or from at least one individual spatial position on the distal array end surface of the unitary array after initial illumination with light energy of a pre-determined wavelength. The light energy emitted or reflected from each fixed probe position individually is collected using a CCD video camera using standard frame grabbing technology and image processing capabilities. Each spectral response detected as emerging light energy by the detector of the CCD is recorded; and the pattern of fluorescence or color is shown either as energy wavelength or as light intensity pixels on the detector representing the spatial dimension. By definition, a pixel is a picture element—a sensitive region—which determines light intensity and/or light energy quantum.

Experimental Series A

Example 2

Single Optical Fiber Strand Preparation

The distal and proximal faces of several single optical fiber strands are polished and cleaned. Each strand's distal end was silanized in 10% (amino) propyltriethoxysilane in acetone v/v). The single core fiber strands were removed after 2 hours rinsed with acetone and then air dried for 30 minutes. The single core strands were placed in a 1.25% gluteraldehyde solution in 0.02 M phosphate buffer (pH 6.8) for 30 minutes. The single core fiber strands then were rinsed with distilled water and placed in 3% polyethyleneimine (PEI) in 0.02 M phosphate buffer (pH 6.8). Finally, the single core strands were air dried for 1 hour, rinsed, and stored in distilled water until being functionalized individually with oligonucleotides.

Oligonucleotide Preparation 10 nmoles of 5-amino-terminal oligonucleotide were dissolved in 90 $\mu$L of 0.1 sodium borate buffer.(SBB). Oligonucleotide activation was initiated by adding 5 nmoles of cyanuric chloride in 10 uL of acetonitrile. The reaction proceeded a room temperature for 1 hour. Unreacted cyanuric chloride was removed by three cycles of centrifugal ultrafiltration (3000 d MW cutoff Microcon 3, Amicon) and diluted with 200 $\mu$L of 0.1 M SBB. The activated primers were recovered in approximately 50 $\mu$L of 0.1 M SBB and stored at 4° C. Primers were used within one month of activation.

Sincile Core Fiber Sensor Preparation

The modified distal end of each single core strand was washed by dipping several times in five-2 ml changes of 0.1 M SBB. The distal strand tips were immersed in a 10 $\mu$L solution of 150 $\mu$L cyanuric chloride-activated oligonucleotide in 0.1 M SBB for 1–2 hours. The fiber strand tips were then immersed in 200 $\mu$L of 90% DMSO, 10% 1 M SBB buffer pH 8.3, 0.1 M succinic anhydride for 1 hour at room temperature. The fiber tips were washed (as described above) with 2 changes of 0.1 M SBB, 5 changes of TE (10 mMTris-HCl pH 8.3, 1 mM EDTA) containing 0.1 M NaCl and 0.1% SDS. Fibers tips were stored in the washing buffer until use.

Bundled Optical Fiber Array Preparation

To make a bundled optical fiber array, seven functionalized 200 $\mu$M diameter single core fiber strands were bundled together. The distal end surface of each fiber strand was first functionalized as described herein with a different cytokine oligonucleotide as a fixed probe—the bundling of seven individual strands creating a multi-target sensing array. The proximal ends of the bundled optical fiber array were epoxied into a 1 mm stainless steel tube (A) and placed into the fiber chuck of the epifluorescence imaging system as shown in FIG. 15. The bundled optical fiber array was three feet long in length and was used for remote sensing (B). The protective rubber tubing is removed from the distal end of the bundled arrays to enable individual functionalization (C).

Primary PCR Reaction

A 176 base pair region from a human IL-4 cDNA plasmid clone [Yokota et al., Proc. Natl. Acad. Sci. USA 83 5894-5898 (1986)] was amplified using primers IL4-U (5-CATC.GTTAGCTTCTCCTGA-3') (SEQ ID NO:1) and IL4-L (5 AAAGTTTTGATGATCTCCTGTA-3') (SEQ ID NO:2) generating a double-stranded PCR product. Conditions for the reaction were 10 mM Tris-HCl pH 8.3, 50 mM KCl, 2.5 mM MgCl2, 0.5% Tween-20, each primer at 0.5 $\mu$M dNTPs, 2 U AmpliTaq polymerase, $10^4$ copies of BamHI-cleaved pcd-hIL-4. Thermocycling parameters were 35 cycles consisting of 10 seconds at 94° C., 10 seconds at 55° C., and 30 seconds at 72° C.

Secondary PCR Reaction

The double-stranded primary amplification products were internally labeled during an asymmetric PCR step using fluorescein-labeled dGTP. Conditions for the reaction were 10 mM Tris-HCl pH 8.3; 50 mM KCl, 2.5 mM $MgCl_2$, 0.5% Tween-20, 1 $\mu$M unlabeled primer IL-4 L, 50 $\mu$M each dATP, dCTP, dTTP, 25 $\mu$M dGTP, 25 $\mu$M fluorescein-labeled dGTP. After asymmetric amplification, the reaction was extracted with phenol and isobutanol. Primers and nucleotides were removed by two cycles of centrifugal ultrafiltration (Microcon 30, Amicon 400 pL TE per wash). Samples were recovered from the filtration unit in 50 μL of TE.

PCR Product Assay

The bundled array distal end was placed in 5 μL of 16 nM labeled PCR product in buffer (TE containing 0.1% SDS and 0.35 M NaCl) for 20 minutes then rinsed with buffer solution (TE containing 0.1% SDS and 0.35 M NaCl). Signal was acquired while the biosensor array was in buffer solution.

Fluorescence Measurements (IP Lab Spectrum). The results are shown by FIG. 20. The images of the bundled array biosensor in buffer solution as acquired by a CCD camera are shown by FIGS. 16A and 16B. The image with white light transmitted through the distal end of the array is demonstrated by FIG. 16A. In comparison, a background fluorescence image at 530 nm taken with 490 nm excitation in buffer solution is shown by FIG. 16B. While there is some light transmitted through the cladding, there is no fluorescence observed across the distal end surface of the bundled array,

TABLE E1

| Probe Sequences | Target Sequences |
|---|---|
| β-glo(+) (segment of human β-globin) | β-glo(+)-CF |
| 5'-(NH$_2$—(CH$_2$)$_6$—)DTT TTT TTT TCA ACT TCA TCC ACG TTC ADD-3' | 5'-Fluorescein-TG AAC GTG GAT GAS GTT G-3' |
| (SEQ ID NO:3) | (SEQ ID NO:4) |
| IFNG (interferon gamma 1) | IFNG-CF |
| 5'-(NH$_2$—(CH$_2$)$_6$—)T12-TGG GTT CTC TGG GCT GTT ACT-3' | 5'-Fluorescein-AG TAA CAG CCA AGA GAA CCC AAA-3' |
| (SEQ ID NO:5) | (SEQ ID NO:6) |
| IL2 (interleukin-2) | IL2-CF |
| 5'-(NH$_2$—(CH$_2$)$_6$—)T12-TA CAA GAA TCC CAA ACT CAC CAG-3' | 5'-Fluorescein-CT GGT GAG TTT GGG ATT CTT GTA-3' |
| (SEQ ID NO:7) | (SEQ ID NO:8) |
| IL4 (interleukin 4) | IL4-CF |
| 5'-(NH$_2$—(CH$_2$)$_6$—)T12-CC AAC TGC TTC CCC CTC TGT-3' | 5'-Fluorescein-AC AGA GGG GGA AGC AGT TGG-3' |
| (SEQ ID NO:9) | (SEQ ID NO:10) |
| 1L6 (intereukin-6) | IL6-CF |
| 5'-(NH$_2$—(CH$_2$)$_6$—)T12-GT TGG GTC AGG GGT GGT TAT T-3' | 5'-Fluorescein-AA TAA CCA CCC CTG ACC CAA C-3' |
| (SEQ ID NO:11) | (SEQ ID NO:12) |

Fluorescence measurements were acquired with a modified Olympus epifluorescence microscope/charged coupled device camera described previously herein.

Experiment 1 The Biosensor

To create probes for a DNA biosensor array, probes specific for human cytokine mRNA sequences were immobilized on the tips of single core optical fibers. Cytokines are powerful immune system hormones whose expression is stimulated in response to inflammatory stimuli or infection. For this reason, there is widespread interest in the regulation of the cytokine gene expression. The sequences of the cytokine probe and targets used are shown in Table E1.

To make a bundled optical fiber array, seven functionalized 200 μM diameter single core fibers were combined and bundled together using epoxy. The distal end surface of each optical fiber strand was first functionalized as described above with a different cytokine oligonucleotide as a fixed probe; and then the bundling of seven functionalized strands created a multi-target sensing array. The proximal ends of the bundled optical fiber array were then epoxied into a 1 mm stainless steel tube and placed into the fiber chuck (A) of the epifluorescence imaging system as shown in FIG. 15. The bundled array was three feet long in length and was used for remote sensing (B). The protective rubber tubing is removed from the distal end of the bundled array to enable individual functionalization (C).

The bundled array of optical fibers was then tested by placing the distal end of the bundled strand sensor into a solution containing one or more 5'fluorescein-labeled cytokine sequences. The bundled array was removed from the target solution after incubation for 5 minutes and rinsed with buffer solution (TE, 0.1% SDS, 0.1 M NaCl). The bundled array was then placed in buffer solution and fluorescence signals were acquired (excitation wavelength 490 nm, emission wavelength 530 nm). Signal analysis was performed in less than 30 seconds with commercially available software Experiment 2

Background-subtracted mean fluorescence intensities were then obtained with IL-4 probe on the sensor. The bundled strand biosensor array was tested in different target solutions employing the sequences of probes and targets shown in Table E1. The biosensor was placed in a target solution for 5 minutes; rinsed with buffer solution (TE containing 0.1% SDS and 0 1 mM NaCl); and fluorescent images were then acquired with the fiber tip in the buffer. The result is shown by FIG. 17. The bundled strand array was dipped in 90% formamide in TE between each test to remove any hybridized target and to regenerate the sensor. The IL4 target solution contained flurescein labeled oligonucleotide complementary to the IL-4 probe on the sensor. After hybridization and read-out, the sensor was regenerated and used to test the IL-2 and IFNG-target solutions containing fluorescein labeled targets that are not complementary to the IL-4 probe. As seen in FIG. 17, these targets do not hybridize to the sensor. The second IL-4 hybridization afforded a signal close to the original test.

Plots of background subtracted mean fluorescence at 530 nm were then taken with 490 nm excitation as a function of time using a 500 μm diameter single core sensor with β-glo probe. A kinetic study using 1 μM, β-glo target solution is shown by FIG. 18. Also a kinetic study using 0.1 gM β-glo target solution is shown by FIG. 19. The sensor was placed in each of the β-glo target solutions for a given time; rinsed with buffer solution (TE containing 0.1% SDS and 0.1 M NaCl); and a fluorescence signal was acquired with the sensor in buffer solution. After data acquisition, the fiber optic array biosensor was placed back in the target solution for an allotted time, rinsed, and examined in buffer. Once the kinetic data was acquired, the hybridized target was removed with 90% formamide in TE to regenerate the sensor.

Fluorescent images using the fiber optic biosensor array were acquired in buffer solution after treatment with IL2 target (A); IL4 target (B); IL6 target (C); β-glo target (D);

IFNF target (E): and a mixture of IL4, IFNG and β-glo targets. The biosensor array distal end was placed sequentially in a fluid (A)–(F) using a 1 μM solution in TE containing 0. 1% SDS and 0.1 M NaCl for 5 minutes; and was then rinsed with buffer solution (TE containing 0.1% SDS and 0.1 M NaCl). Hybridized oligonucleotides were removed after each immersion and optical detection using a 90% formamide solution in TE after each analysis. As shown by FIG. 20, the specificity of each probe-target hybridization (A)–(F) was confirmed. The signals obtained in buffer before hybridization were subtracted from the signals obtained after hybridization. High intensities are signified with white light.

The background subtracted mean fluorescence signals from FIG. 20 are shown in graph form by FIG. 21. Note: When a combination of oligonucleotide targets was placed in solution the signal obtained was comparable to the signal obtained when a single target was in the solution. FIGS. 20 and 21 in combination reveal that high signals were only observed on those fibers carrying probes complementary to the added target, demonstrating that hybridization to the fiber is also highly specific.

Experiment 3

Hybridization competition between labeled and unlabeled variations of the same target sequences were performed using the biosensor array. Increasing concentrations of unlabeled targets were added to 1 μM solutions of a labeled identical target. The optical fiber biosensor was placed in the mixture of labeled and unlabeled target solution for 10 minutes; rinsed with buffer solution, and the background-subtracted fluorescence image was acquired while the distal array tip was in the buffer solution. The distal tip was rinsed with 90% formamide in TE between test samples to remove the hybridized target. The results are shown by FIG. 22; the fluorescence decrease was directly proportional to increasing concentration of sample target.

Experiment 4

A practical application of the fiber optic biosensor is shown by the assay of cDNA samples generated by reverse-transcription PCR (RT-PCR) [Egger, et al J. Clin. Microbiol. 33: 142 (1995)]. A 176 base pair fragment containing the IL-4 probe sequence (Table E1) was amplified from a cloned IL-4 cDNA target and internally labeled with fluorescein using an asymmetrical PCR procedure [Cronin et al., Human Mutation 7: 244–255 (1996)]. The cytokine sensor array was dipped directly into the purified PCR reaction mixture. Using 5 μL of a 16 nm PCR target solution the sensor gave a clear, detectable, specific signal after 20 minutes.

Optimization of the System

Immobilized probe concentrations limit the amount of complementary target that can hybridize to the probe and generate a signal. The feasibility of detecting a fluorescein labeled target in-situ hybridization to the immobilized probe on the distal surface was tested first using a 500 um diameter single core fiber with an immobilized IL-4 probe (Table E-1). The tips of the array (surface area 0.002 $cm^2$) were placed in the target solution, which can be as small as 3 L in a 0.4 mL eppendorf tube. The detection system consists of a modified epifluorescence microscope with the optics optimized to couple with an optical fiber.

The detection system parameters were also optimized. Increasing the acquisition time improved the signal however, the increased exposure time caused photo bleaching and adversely affected subsequent sensor use. A two second acquisition time was found to be optimal in maximizing the detection while minimizing photo bleaching of the fluorescein-labeled target. This fiber optic biosensor system has a detection limit of 10 nM.

Characterization of the Sensor

The sensor's specificity was evaluated by placing the sensor in complementary and non-complementary-labeled target solutions. The fluorescent signal increases upon exposure to the complementary labeled target. The complete absence of signal when the biosensor was placed in a noncomplementary labeled targets confirmed the hybridization specificity (FIG. 17). Lengthy incubation times are frequently a concern in hybridization experiments utilizing immobilized probes. The optical fiber biosensor described here shows excellent hybridization kinetics. Hybridization is 85% complete after 1 minute using a 1-uM target solution (FIG. 18). With a 0.1-μM target solution, hybridization is 90% complete after 15 minutes (FIG. 19). The 10-nM target solution required 10 minutes to generate a clear signal (data not shown). The fiber biosensors can be regenerated repeatedly by dipping the distal array tip in 90% formamide in TE buffer (10 mM Tris-HCl pH 8.3, 1 mM EDTA) for 10 seconds at room temperature. The biosensor then gives an original comparable signal for all subsequent analyses with alternative complementary oligonucleotide target (FIG. 17). Heating the formamide solution to 45° C. was also effective and did not compromise sensor integrity.

The biosensor offers significant advantages for hybridization analysis. The optical fiber array serves as the hybridization support and also facilitates sensitive quantitative fluorescent detection of in-situ hybridization using a very low sample volume. Multiple synthetic oligonucleotide probes were covalently immobilized and fixed on one end of a 200 μm diameter optical fiber.

The fiber optic biosensor and methodology demonstrates a fast, reproducible, highly sensitive and durable system for the specific identification of DNA sequences. Fiber optic biosensor arrays enable simultaneous detection of multiple DNA sequences with reduced assay time and increased convenience. Complete analysis of multiple DNA sequences can be accomplished in under 5 minutes. Biosensors can be prepared in advance and be stored at 40° C.; these maintain their sensing capabilities for many months. The biosensor's small size also offers the ability to perform hybridization analysis on large numbers of target sequences using extremely small sample volumes. The biosensor is also, useful for performing in-situ hybridization analyses in settings where conventional hybridization methods would be difficult, if not impossible, to implement.

Experimental Series B

Experimental Protocol

The approach to DNA immobilization involves the site-selective photodeposition of an acrylamide and N-acryloxysuccinimide copolymer. The distal face of a fiber optic imaging array is first functionalized with 3-trimethoxysilylpropylmethacrylate to attach the photopolymerizable acrylate to the glass and surface allowing for the covalent attachment of polymer matrices to the distal face. The proximal array end surface of the unitary array is placed on a photodeposition system which allows for site-positioned illumination of the proximal array end. The distal end of the functionalized array is then dip coated with a thin film of an acrylamide/acryloxysuccinimide prepolymer containing a photoinitiator. The prepolymer is then photopolymerized by light illumination through the fiber for a fixed time and excess prepolymer is removed by rinsing with ethanol. After the polymer matrix is deposited, the distal end is placed in a solution of a 5'-amino-terminated oligonucleotide. As the polymer then hydrates, the oligonucleotide reacts with the succinimidyl ester residue, thereby covalently immobilizing the oligonucleotide. The residual reactivity of the esters is capped by placing the distal end in a 1 mM ethanolamine buffer solution, pH 8.5. The process is subsequently repeated to immobilize other oligonucleotide probes. Once fabricated the DNA sensor array is connected to a modified epifluorescence microscope (Olympus) with computer-controlled excitation and emission filter wheels and a frame-transfer charge coupled device (CCD) camera (Photometries) as previously described herein.

Experiment 5

Initial studies were performed using a poly (dA) sensor array comprised of both an immobilized poly (dA) polymer matrix and a control acrylamide polymer matrix, which was not copolymerized with N-acryloxysuccinimide, using a poly (dT)-FITC target. The biosensor was placed directly in a dilute solution of poly (dT)-FITC. During hybridization of poly (dT)-FITC to the poly (dA) polymer matrix, poly-FITC concentrates in the polymer matrix resulting in an increase in fluorescence over the background solution fluorescence. The acrylamide matrix thus serves as a control for non-specific absorption of target. After hybridization to the poly (dT)-FITC, the poly (dA) biosensor array could be regenerated by immersing in 65° C. buffer for 15 minutes after hybridization. This procedure completely dehybridized the probe/target duplex. Table E2 lists the oligonucleotide probes used in this study along with the complementary target sequences.

amplification. However, PCR samples can be biotinylated during the amplification which decreases the time to analysis and minimizes sample contamination. The detection procedure involves hybridization with a biotinylated nucleic acid target followed by label juncture with streptavidin-FITC.

Accordingly, calibration of the poly (dA) matrix with poly (dT)-Biotin; and hybridization was carried out for 20 minutes at 0.2, 2.0 and 19.6 nM followed by development with streptavidin-FITC. The results are shown by FIG. 26 which plots the mean fluorescence intensity of the poly (dA) matrix versus the log of poly (dT)-biotin concentration. As in a diffusion controlled system, the fluorescence intensity is shown to be linear with the log poly (dT)-biotin concentration from 0.2–20 nM. This system has a detection limit approximately an order of magnitude lower in target concentration for the same in-situ hybridization time. This improvement is due to the multiple FITC labels on each streptavidin molecule and the absence of photo bleaching during hybridization that otherwise occurs with FITC-labeled oligonucleotides. The technique has a detection limit of 0.2 nM which is approximately an order of magnitude lower than other DNA biosensors.

Experiment 7

In order to test if the DNA biosensor could distinguish single point mutations, an array comprised of multiple H-ras wild type probes (H-ras Wt.) and multiple mutant probes with a single base difference (H-ras Δ) was fabricated. A FITC-labeled mutant (Δ-FITC) target was hybridized to the

TABLE E2

| Probe Name (code) | Sequence 5'-3' | Sequence 5'-3' | Target Name (code) |
|---|---|---|---|
| (p(dA)) | H2N-(A)$_{18}$ | FITC-(T)$_{18}$<br>Biotin-(T)$_{18}$ | (p(dT)-FITC)<br>(p(dT)-biotin) |
| H-ras wild type (H-ras Wt.) | H2N-CCGGCGGTGT (SEQ ID NO:13) | FITC-ACACCGCCGG (SEQ ID NO:14) | Wild type target (Wt-FITC target) |
| H-ras mutant (H-ras Δ) | H2N-GCCGTCGGTGT (SEQ ID NO:15) | FITC-ACACCGACGGC (SEQ ID NO:16)<br>5'-labeled biotin amplicon containing ACACCGACGGC (SEQ ID NO:17) | Mutant target (Δ-FITC target)<br>PRC amplicon<br>Δ PCR 109 bp |

FIG. 23 shows the fluorescence increase of the poly (dA) matrix upon repeat hybridizations to poly (dT)-FITC; and shows three repeat hybridizations after regenerating the poly (dA) sensor array with 65° C. buffer. The signal increases are essentially the same for all three hybridizations when the decrease in solution fluorescence is taken into account as measured with the acrylamide matrix control. The plot demonstrates that sensor regeneration occurs in less than 10 seconds, simplifying and speeding up the testing procedure.

The poly (dA) biosensor array was then tested for its time response to various concentrations of pCly (dT)-FITC. This data is shown by FIG. 24. The sharp decrease between standards represents the biosensor regeneration with 65° C. buffer. Other determinations were then made. FIG. 25 plots the initial hybridization rate versus poly (dT)-FITC concentration. The poly (dA) sensor array shows a linear response from 1.3–130 nM with an R2 value of 0.99 demonstrating that the rate of hybridization is directly proportional to the concentration of the target oligonucleotide. This linearity indicates that the response time of the DNA sensor array is diffusion controlled; and that the oligonucleotide probes are immobilized on the surface of the polymer matrix; allowing for solution-type kinetics.

Experiment 6

A different labeling procedure was developed to increase the array's sensitivity and expand its generality. Presently PCR samples for fluorescence analysis must be labeled after DNA sensor array at 28° C. in low stringency buffer, 2×SSPE. The Δ-FITC target is the perfect complement for the immobilized H-ras A. The low stringency buffer condition was insufficient to distinguish the non-complementary oligonucleotide target at 28° C.

As temperature is often utilized to distinguish non-complementary targets, thermal studies were then undertaken to determine the melt characteristics of the duplexes. The distal array end of the biosensor was immersed in buffer solution and the temperature was raised while monitoring fluorescence FIG. 27 shows the melting curves of the DNA sensor array after hybridization at 28° C. with the A-FITC target. The plot shows that Tm for the H-ras Wt./Δ-FITC target duplex occurs at approximately 42° C. while the Tm for the perfect complement duplex H-ras/Δ-FITC target occurs at 550 C. The data shows that if hybridization is performed at approximately 54° C., only the complementary target will hybridize.

FIGS. 28A and 28B respectively show fluorescence images of the DNA sensor array after hybridization with the A-FITC target at 28° C. and 54° C. A and B respectively. The images indicate that the DNA sensor array can distinguish a point mutation when hybridization is conducted at 54° C. Images were acquired at 490 nm. The DNA sensor array was then calibrated with the Δ-FITC target by the same procedure used for the poly (dA) sensor array and poly (dT)-FITC with the exception that hybridizations were carried out at 54° C. FIG. 29 shows hybridization data for the DNA sensor array to 196 nM Δ-FITC target at 54° C. The Hras Wt. matrix showed no response to the H-ras Δ-FITC target. FIG. 30 is a plot of the Δ target calibration curve for the data of FIG. 29 which demonstrates the sensitivity of the sensor in the concentration range 2.0 to 196 nM.

Experiment 8

In order to test the array's ability to distinguish point mutations of amplified DNA, a PCR sample containing the target sequence was obtained. The target sample, biotinylated during PCR amplification, was first determined and diluted; allowed to hybridize to the DNA sensor array for 20 minutes at 54° C.; washed and then labeled by juncture to streptavidin-FITC.

FIG. 31 shows a fluorescence image of the DNA sensor array after a 20 minute hybridization to a biotinylated Δ PCR amplification at 54° C., followed by a 5 minute streptavidin-FITC development. The image was acquired at 490 nm excitation, 530 nm emission. The image of FIG. 31 demonstrates that the biosensor can distinguish single base mutations in amplified DNA.

In summary, a fiber optic DNA sensor array has been fabricated by photodeposition of amine-reactive polymer matrices on an imaging fiber optic array; and 5 aminoterminal oligonucleotides have been covalently immobilized as multiple fixed probes through amide bond formation with the succinimidyl ester residues of the polymer matrices. This fiber optic DNA sensor array is capable of simultaneously monitoring multiple hybridization events. The DNA sensor array also has the added advantage of simultaneously evaluating a fluid mixture of target oligonucleotides with multiple kinds of probe oligonucleotides with real-time monitoring. The DNA sensor array can be utilized to identify a single point mutation of Ras oncogene PCR product: and the sensor optically detected point mutations at DNA concentrations of 0.2–196 nM following a 20 minute hybridization. Lower concentrations of target oligonucleotides could be detected by hybridizing for longer times. The biosensor's small size (350 μm o.d.) and the small volume of the individual array elements (20 pL) enable sub-microliter sample volumes to be analyzed, increasing the value of the sensor.

The present invention is not to be restricted in form nor limited in scope except by the claims appended here.

---

We claim:

1. An optical sensor for detecting nucleic acids in a fluid sample comprising:
   a) a preformed, unitary fiber optic array comprising a plurality of optical fiber strands, said strands being disposed co-axially and joined along their lengths, said fiber optic array having a proximal and distal end, each of said ends being formed by multiple strand faces of said strands, at least one of said array ends presenting a discrete fiber optic array surface for introduction and conveyance of light energy; and
   b) at least a first and a second nucleic acid attached to a first and second portion, respectively, of said distal array end, said first nucleic acid being optically coupled to and in optical communication with a first of said multiple end faces at said distal array end, and said second nucleic acid being optically coupled to and in optical communication with a second of said multiple end faces at said distal array end.

2. A sensor according to claim 1 wherein said nucleic acid is selected from the group consisting of DNA, RNA and PNA.

3. A sensor according to claim 1 wherein said preformed unitary array is selected from the group consisting of an imaging fiber, a coherent fiber array, a random fiber array, and a semi-random fiber array.

4. A sensor according to claim 1 further comprising a light source.

5. A sensor according to claim 1 further comprising a light detector.

6. A sensor according to claim 1 wherein said nucleic acid is attached to said portion by introducing light energy to at least said first end face in the presence of a photoactivatable compound.

7. A sensor according to claim 6 wherein said photoactivatable compound is selected from the group consisting of acrylamide, N,N-methylene bis(acrylamide), hydroxyehtylmethacrylate, EGDMA, vinyl acetate, N-(3-aminopropyl)methacrylamide, hydrochloride, and N-acryloxysuccinimide.

8. A sensor according to claim 6 wherein said light energy is introduced at said proximal end.

9. A sensor according to claim 6 wherein said light energy is introduced at said distal end.

10. A method of making a fiber optic sensor comprising:
    a) providing a preformed, unitary fiber optic array comprising a plurality of optic fiber strands disposed co-axially and joined along their lengths, said fiber optic array having a proximal and a distal array end, each of said ends being formed of multiple strand end faces and at least one of said array ends presenting a discrete optic array surface for introduction and conveyance of light energy;
    b) contacting at least a first nucleic acid and a photoactivatable compound with at least a first proximal optic fiber strand end face; and
    c) attaching said first nucleic acid to said end face by introducing light energy to said first optic fiber strand.

11. A method according to claim 10 further comprising:
    d) contacting at least a second nucleic acid and a photoactivatable compound with at least a second proximal first optic fiber strand end face; and
    e) attaching said second nucleic acid to said second end face by introducing light energy to said second optic fiber strand.

12. A method according to claim 10 wherein said light energy is introduced into the first optic fiber strand at the distal end.

13. A method according to claim 10 wherein said light energy is introduced at said proximal end.

14. A method according to claim 10 wherein said nucleic acid is selected from the group consisting of DNA, RNA and PNA.

15. A method according to claim 10 wherein said introduction utilizes a light source and a mask for illuminating a portion of said array end surface for precisely controlling the location and size of said nucleic acid attachment.

16. A method of detecting at least one target sequence in a fluid sample comprising:
    a) providing a a preformed, unitary fiber optic array comprising a plurality of optic fiber strands disposed co-axially and joined along their lengths, said fiber optic array having a proximal and a distal array end, each of said ends being formed of multiple strand end faces and at least one of said array ends presenting a discrete optic array surface for introduction and conveyance of light energy, said distal array end comprising a plurality of nucleic acid probes, each of which is attached to a different strand end face;
    b) contacting said distal end of said array with said sample; and
    c) detecting the presence of a target sequence.

17. A method according to claim 16 wherein said target sequence is labeled and said detecting is done by illuminating said label with excitation light energy and detecting emission light energy from said label.

18. A method according to claim 17 wherein said illuminating is done at said proximal end of said array.

19. A method according to claim 17 wherein said illuminating is done at said distal end of said array.

* * * * *

SEQUENCE LISTING

<160> NUMBER OF SEQ ID NOS: 17

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: synthetic

<400> SEQUENCE: 1
catcgttagc ttctcctga                                                19

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 2
aaagttttga tgatctcctg ta                                            22

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: synthetic

<400> SEQUENCE: 3
dttttttttt caacttcatc cacgttcadd                                    30

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: synthetic

<400> SEQUENCE: 4

-continued

```
tgaacgtgga tgasgttg                                             18

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: synthetic

<400> SEQUENCE: 5
tgggttctct gggctgttac t                                         21

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: synthetic

<400> SEQUENCE: 6
agtaacagcc aagagaaccc aaa                                       23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: synthetic

<400> SEQUENCE: 7
tacaagaatc ccaaactcac cag                                       23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: synthetic

<400> SEQUENCE: 8
ctggtgagtt tgggattctt gta                                       23

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 9
ccaactgctt cccctctgt                                            20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 10
acagaggggg aagcagttgg                                           20

<210> SEQ ID NO 11
<211> LENGTH: 21
<212> TYPE: DNA
<213> ORGANISM: Artificial Sequence
```

```
<220> FEATURE:
<223> OTHER INFORMATION: Description of Artificial Sequence: synthetic

<400> SEQUENCE: 11
gttgggtcag gggtggttat t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: synthetic

<400> SEQUENCE: 12
aataaccacc cctgacccaa c                                              21

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: synthetic

<400> SEQUENCE: 13
ccggcggtgt                                                           10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: synthetic

<400> SEQUENCE: 14
acaccgccgg                                                           10

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: synthetic

<400> SEQUENCE: 15
gccgtcggtg t                                                         11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: synthetic

<400> SEQUENCE: 16
acaccgacgg c                                                         11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: synthetic

<400> SEQUENCE: 17
acaccgacgg c                                                         11
```